US008344177B2

(12) United States Patent
Neri et al.

(10) Patent No.: US 8,344,177 B2

(45) Date of Patent: Jan. 1, 2013

(54) ALBUMIN BINDING MOLECULES AND USES THEREOF

(75) Inventors: Dario Neri, Buchs (CH); Christoph Dumelln, Cambridge, MA (US)

(73) Assignee: Philochem AG (CH)

( * ) Notice: Subject to any disclaimer, the term of this patent is extended or adjusted under 35 U.S.C. 154(b) by 524 days.

(21) Appl. No.: 12/513,436

(22) PCT Filed: Nov. 2, 2007

(86) PCT No.: PCT/IB2007/004213

§ 371 (c)(1),
(2), (4) Date: Feb. 25, 2010

(87) PCT Pub. No.: WO2008/053360

PCT Pub. Date: May 8, 2008

(65) Prior Publication Data

US 2010/0172844 A1 Jul. 8, 2010

(30) Foreign Application Priority Data

Nov. 3, 2006 (GB) .................................. 0621973.7

(51) Int. Cl.
*C07C 229/04* (2006.01)
*A61K 31/195* (2006.01)

(52) U.S. Cl. ........ 562/450; 562/442; 562/444; 514/563; 514/564

(58) Field of Classification Search .................. 562/442, 562/444, 450; 514/563, 564
See application file for complete search history.

(56) References Cited

U.S. PATENT DOCUMENTS

| | | | |
|---|---|---|---|
| 6,090,958 | A | 7/2000 | Leone-Bay et al. |
| 6,294,674 | B1 | 9/2001 | Picard et al. |

FOREIGN PATENT DOCUMENTS

| | | |
|---|---|---|
| RU | 2203268 | 4/2003 |
| WO | WO96/34012 | 10/1996 |
| WO | WO 00/31536 | 6/2000 |
| WO | WO 03/045378 | 6/2003 |

OTHER PUBLICATIONS

Oyman, Chimica Acta Turcica, 1974, 2(1), 65-81(RN 53668-54-5 only).*

Oyman, Chimica Acta Turcica, 1974, 2(1 ), 65-81.*

Knütter, et al., "Analysis of the Transport Properties of Side Chain Modified Dipeptides at the Mammalian Peptide Transporter PEPT1," European Journal of Pharmaceutical Sciences 21 (2004) pp. 61-67 (8 pages).

Nishimori, et at, "Carbonic Anhydrase Inhibitors: DNA Cloning and Inhibition Studies of the α-Carbonic Anhydrase from Helicobacter Pylori, A New Target for Developing Sulfonamide and Sulfamate Gastric Drugs," J. Med. Chem. (2006), 49, pp. 2117-2126 (10 pages).

Stranix, et al., "Lysine Sulfonamides as Novel HIV-Protease Inhibitors: Optimization of the Nϵ-Acyl-Phenyl Spacer," Bioorganic & Medicinal Chemistry Letters 13 (2003) pp. 4289-4292 (4 pages).

Koehler, et al., "Albumin Affinity Tags Increase Peptide Half-Life In Vivo," Bioorganic & Medicinal Chemistry Letters 12 (2002) pp. 2883-2886 (4 pages).

Hatzidakis, et al., "Use of L-Lysine Fluorescence Derivatives as Tracers to Enhance the Performance of Polarization Fluoroimmunassays. A Study Using Two Herbicides as Model Antigens," Anal. Chem. (2002), 74, pp. 2513-2521 (10 pages).

Written Opinion of the International Preliminary Examining Authority mailed Jan. 15, 2009, issued in connection with International Patent Appln. No. PCT/IB2007/004213 (5 pages).

Patent Compound Registry No. 543347, Patent Chemistry Database, Jan. 12, 2009 (1 page).

Patent Compound Registry No. 5777256, Patent Chemistry Database, Jan. 12, 2009 (1 page).

Patent Compound Registry No. 5051795, Patent Chemistry Database, Jan. 12, 2009 (1 page).

Patent Compound Registry No. 6865539, Patent Chemistry Database, Jan. 12, 2009 (1 page).

Patent Compound Registry No. 1308028, Patent Chemistry Database, Jan. 12, 2009 (1 page).

Beilstein Registry No. 7222615, CrossFire Beilstein Database, Jan. 12, 2009 (2 pages).

Beilstein Registry No. 2657511, CrossFire Beilstein Database, Jan. 12, 2009 (6 pages).

Beilstein Registry No. 2995035, CrossFire Beilstein Database, Jan. 12, 2009 (1 page).

Beilstein Registry No. 6302003, CrossFire Beilstein Database, Jan. 12, 2009 (1 page).

Beilstein Registry No. 9729928, CrossFire Beilstein Database, Jan. 12, 2009 (1 page).

Chapman, Kevin T., et al., "Inhibition of Matrix Metalloproteinases by P1 Substituted N-Carboxyalkyl Dipeptides", Biorganic & Medicinal Chemistry Letters, Jan. 1996, vol. 6, No. 3, pp. 329-332.

Shiosaki, Kazumi, et al., "Development of Potent and Selective CCK-A Receptor Agonists from Boc-CCK-4: Tetrapeptides Containing Lyn(N )-Amide Residues", Journal of Medicinal Chemistry, Jan. 1, 1992, vol. 35, No. 11, pp. 2007-2014.

Pacofsky, Gregory J., et al., "Potent Dipeptide Inhibitors of the pp60c-src SH2 Domain", Journal of Medicinal Chemistry, Jan. 1, 1998, vol. 41, No. 11, pp. 1894-1908.

Gunther, Robert, et al., "Protease Catalysis Mediated by a Substrate Mimetic: A Novel Enzymatic Approach to the Synthesis of Carboxylic Acid Amides", Chemistry—A European Journal, Jan. 1, 2000, vol. 6, No. 3, pp. 463-467.

Nishizawa, Rinzo, et al., "Synthesis and Structure—Activity Relationships of Bestatin Analogues, Inhibitors of Aminopeptidase B", Journal of Medicinal Chemistry, Jan. 1, 1977, vol. 20, No. 4, pp. 510-515.

Communication from European Patent Office, 2012.

* cited by examiner

*Primary Examiner* — Shailendra Kumar

(74) *Attorney, Agent, or Firm* — McCarter & English

(57) ABSTRACT

The invention relates to portable albumin binders, which are useful for improving the pharmacokinetic properties of diagnostic or therapeutic agents, in particular increasing the blood circulations time and/or the tissue penetration capacity of such agents.

36 Claims, 20 Drawing Sheets

| Molecule # | Structure | Molecule # | Structure |
|---|---|---|---|
| 326 |  | 536 |  |
| 428 |  | 539 |  |
| 533 |  | 624 |  |
| 535 |  | 622 |  |
| 625 |  | 630 |  |
| 631 |  | 632 |  |

A

428-Lys-FITC:

B

428-Lys-FAM:

C

428-Lys-β-Ala-DTPA-Gd:

a

428-D-Lys-Ac 1 7

X-D-Lys-Ac

| Inhibitor | Binding site | 1 µM | 10 µM | 100 µM |
|---|---|---|---|---|
| Warfarin | I | 147 | 124 | 138 |
| Phenylbutazone | I | 130 | 146 | 113 |
| Indomethacin | I | 141 | 101 | 59 |
| Ibuprofen | II | 128 | 91 | 65 |
| Dansylsarcosine | II | 132 | 98 | 72 |
| Diazepam | II | 142 | 118 | 81 |
| L-Tryptophane | II | 144 | 143 | 132 |
| Myristic acid | Fatty acids | 103 | 42 | 31 |
| $CuSO_4$ | Metal ion | 137 | 143 | 135 |

| Controls | FP |
|---|---|
| No competitor | 144 |
| No HSA | 33 |

ALBUMIN BINDING MOLECULES AND USES THEREOF

CROSS-REFERENCE TO RELATED APPLICATIONS

This application is a U.S. National Phase Application under 35 U.S.C 371 of International Application No. PCT/IB2007/004213 filed Nov. 2, 2007, which claims the benefit of GB 0621973.7 filed Nov. 3, 2006, the disclosures of which are expressly incorporated herein by reference in their entirety.

FIELD OF THE INVENTION

The invention relates to portable albumin binders, which are useful for improving the pharmacokinetic properties of diagnostic or therapeutic agents, in particular increasing the blood circulation time and/or the tissue penetration capacity of such agents.

BACKGROUND OF THE INVENTION

Pharmacokinetic properties of drugs are essential determinants of the pharmaceutical action drugs perform within the human body. In most cases, drugs need to be sufficiently long lived within the organism, yielding concentrations in suitable body compartments which are high enough for the display of the desired pharmacological function (e.g., binding of a drug to its receptor).

In many cases, desired pharmacokinetic properties of small drugs are a result of a certain binding capacity to albumin, which is the most abundant protein in blood, at concentrations of approx. 600 μM. Pharmaceutical companies can empirically screen for suitable albumin binding characteristics of their drug of interest. However, this approach is of limited utility, as in most cases the albumin binding properties of the molecule are intimately connected to the portion of the molecule responsible for the desired pharmacological action.

Though many albumin binding molecules are thus known, the vast majority of known albumin binders are not "portable", in the sense that they cannot easily be coupled to other bioactive moieties without loss of albumin binding or other relevant pharmaceutical properties. Bromophenol blue and ibuprofen, two very well known molecules in biochemistry and in pharmaceutical sciences, may serve as examples to illustrate the case. Bromophenol blue is an avid albumin binder that forms complexes with albumin which are stable when analyzed by native polyacrylamide gel electrophoresis. However, the relatively complex chemical structure of bromophenol blue lacks suitable functional groups for the easy coupling of this molecule to other molecules of pharmaceutical interest (e.g., small organic drugs or protein drugs). Ibuprofen, one of the most widely used anti-inflammatory agents, binds to albumin with a dissociation constant in the micromolar range. However, as soon as one attempts to modify the carboxylic acid group of the molecule (e.g., by amide bond formation), in order to couple ibuprofen to other moieties of biopharmaceutical interest, ibuprofen loses its albumin-binding affinity.

The long circulation time of albumin has, nonetheless, been exploited for the direct conjugation of drugs to albumin. For example, a number of therapeutic polypeptides have been fused to albumin (EPO, interferons, interleukins, therapeutic peptides) at the genetic levels, and some of the corresponding fusion proteins are being investigated in the clinic [1].

An example is the direct coupling of chemotherapeutic agents to a unique cysteine residue (Cys34) on the surface of human serum albumin. Kratz and colleagues have used either the primary amino group or the carbonyl group of the anti-cancer chemotherapeutic drug doxorubicin for a site-specific coupling of this drug to the Cys34 residue of human albumin. The chemical moieties used as linkers between doxorubicin and albumin were chosen for their ability to be hydrolyzed, thus liberating the pharmacologically active doxorubicin moiety [2]. As a representative example, the maximum tolerated dose of DOXO-EMCH is 2-10 times higher than that of unmodified doxorubicin, and DOXO-EMCH can be injected at 2-10 times the molar equivalent of doxorubicin in tumor-bearing mice, with lower toxicity compared to unconjugated doxorubicin and more potent therapeutic effects. Similar results have been reported with the preformulated doxorubicin-HSA conjugate [3]. This protein derivative is currently being investigated in the clinic [4]. In a similar fashion, the same group has chemically coupled methotrexate to albumin, using a peptide linker which can be preferentially cleaved by matrix metalloproteinases at sites of arthritis in vivo. The corresponding protein-drug conjugate can be considered a prodrug and is currently in pharmaceutical development.

However, a severe general disadvantage of protein-drug conjugates is that they may be immunogenic in humans [5]. Direct conjugation can therefore not be considered a general solution to the problem of finding a means of associating drugs with albumin and thus improving their pharmaceutical properties. A generally applicable solution would be provided by portable albumin binding molecules, i.e. molecules that, on the one hand, have a selective affinity for albumin, and on the other hand may be attached to any drug of interest.

One of the physiological roles of albumin is to act as a carrier of fatty acids. This property has been exploited in order to associate a drug with albumin. For example, a well-known insulin derivative in commerce features a covalent modification of the insulin moiety by amide formation with tetradecanoic acid LEVEMIR®. This long fatty acid chain confers certain beneficial properties to insulin, including prolonged blood clearance, as would be expected considering the fatty acid-binding properties of albumin. However, the disadvantage of this approach is that it is not easily applicable to other molecules. In particular, it is not applicable to less soluble proteins or small drugs, due to the unacceptably low water solubility of the resulting derivative.

Recently, Genentech scientists have reported the discovery and use of disulfide-constrained albumin-binding peptides as a portable tag for altering the pharmacokinetic properties of proteins of biopharmaceutical relevance (e.g., antibody fragments), conferring them long blood circulation time in blood [6]. In a similar fashion, several biotech companies (e.g., Domantis, Affibody) have recently developed mutants of small globular proteins as "portable" albumin binders, in order to confer slow blood clearance properties to pharmaceutical proteins of interest, by genetic fusion [7-10]. However, peptides and proteins are not ideal as vehicles to confer albumin affinity upon drugs. Peptides and proteins are labile molecules that may be destroyed by digestion or denaturation, and are thus, in particular, difficult to administer orally. Such drugs must therefore in general be administered by injection, which is a cause of inconvenience compared to the oral route.

Apart from the field of drugs as such, there is also a need to control and improve the blood retention time and tissue distribution of diagnostic agents, such as diagnostic imaging and contrast agents. Fluorescein is a good example to illustrate such a need. Fluorescein is routinely used in opthalmology for fluoroangiographic imaging procedures, with over a million injections per year in the US and in Europe. Quite surprisingly, fluorescein is not an approved pharmaceutical agent. In most cases, a 3-5 ml fluorescein sodium solution in water (10%) has to be prepared by the physician prior to intravenous injection.

Fluorescein is cleared from the blood very rapidly, and therefore has to be administered at high doses, by bolus injection. However, at such high doses, fluorescein induces nausea and vomit in up to 20% of patients, depending on the patient group. These complications are more frequent in patients from black, Asian, Chino-Asian or mixed ethnic origins [11]. More severe reactions are rare, but include hives, laryngeal edema, bronchospasm, syncope, anaphylaxis, myocardial infarction and cardiac arrest [12].

Extravasation of fluorescein dye during the injection can be a serious complication of angiography. With a pH of the solution of 8 to 9.8, fluorescein infiltration can be quite painful. Sloughing of the skin, localized necrosis, subcutaneous granuloma and toxic neuritis have been reported following extravasation of fluorescein. Although life-threatening reactions during angiography are rare, the possibility that they may arise necessitates that angiographic facility should be properly equipped and prepared to manage serious reactions to the procedure.

Decreasing rate of injection may reduce the risk or severity of side reactions. However, this impairs imaging sensitivity.

There is therefore, e.g., a need for a derivative of fluorescein which is better and longer retained in the vascular space and is, in particular, less prone to either becoming metabolised or extravasation. Such a derivative would allow the administration of lower dosages, thus decreasing the likelihood and severity of side effects and complications, and would moreover lead to improved image quality.

Similar considerations apply to magnetic resonance imaging (MRI) contrast agents. Current extracellular MRI contrast agents are limited by relatively short half-lives and are also freely extravasated into background muscle, which decreases the contrast-to-noise ratio during steady-state imaging. For routine clinical use in MRI and magnetic resonance angiography applications, it is desirable that the contrast agent be selectively retained in the vascular space and have an extended blood half-life in order to provide a sufficient plasma concentration over a 1 hour imaging window. An extended blood half life would be necessary in order to facilitate imaging of multiple body regions and the acquisition of long, pulse-gated scans of coronary arteries [13].

A number of groups have aimed at improving the pharmacokinetic properties of contrast agents such as Gd-DTPA MAGNEVIST®, by coupling this moiety to portable albumin binders. However, the dissociation constants of such albumin binders have been limited to the order of 100 μM [14]. There thus remains a need for improving contrast agents such as Gd-DTPA, e.g., in order to extend their half-lives and improve their relaxation properties.

There is thus considerable interest in the identification and development of small organic molecules which may be used as portable albumin binding moieties for coupling to a wide range of molecules of pharmaceutical interest (e.g., small organic molecule drugs, protein drugs, or diagnostic agents, e.g., for various forms of medical imaging). However, the success of attempts to identify small organic molecules which may be used as portable albumin binders [15], has been limited so far. Particular areas of concern are the strength of binding to albumin, the chemical stability of albumin-binding conjugates in-vivo and the extent of portability (in particular, good pharmacokinetic properties of the conjugate should ideally be achievable with any drug or class of drugs, not only with certain favourable examples of drugs).

There is a need to minimize the size of portable albumin binders in order to allow the development of pharmaceutical agents which do not violate Lipinski's rule of five [16]. Other desired properties of an portable albumin binder include binding selectivity (i.e., discrimination between albumin and other molecules), easy synthetic accessibility, facile conjugation to (bio)pharmaceutical molecules of interest, good water solubility and absence of inherent toxicity. To date, it has not been possible to provide albumin binders that combine these advantageous properties.

SUMMARY OF THE INVENTION

General Description of the Invention

The present invention provides a novel class of albumin-binding compounds and conjugates thereof with molecules of pharmaceutical interest, in particular therapeutic and/or diagnostic agents. Such molecules of pharmaceutical interest may hereinafter be referred to simply as "agents". According to the invention, said compounds and conjugates are capable of binding to albumin, that is, they have affinity for albumin. The compounds and conjugates of the invention may thus hereinafter be referred to collectively as albumin binders. Preferably, the albumin-binding compounds of the invention also bind to albumin selectively, that is, with preference over other binding partners. The compounds are readily prepared, and may conveniently be conjugated (i.e. linked, coupled, covalently bound) to a wide range of other molecules (in particular said agents), by chemical methods known in the art.

When conjugated to a diagnostic or therapeutic agent, the albumin-binding compounds of the invention beneficially alter the pharmacokinetic properties of said agent. In particular, such conjugation according to the invention increases the blood circulation time (alternatively referred to as blood clearance, or blood clearance time), i.e. the physiological half life of the agent. Conjugation to the albumin-binding compounds of the invention allows the agent to be cleared and/or degraded less rapidly, as the agent will, by virtue of the albumin binding moiety according to the present invention, remain in the bloodstream bound to albumin. The above aspects of the invention will be thus be advantageous when applied, e.g., to agents that are rapidly metabolised or otherwise cleared, e.g. macromolecules, in particular antibody fragments or smaller globular binding proteins, or any other agent or molecule for which more effective and longer retention in the bloodstream is desirable, e.g., fluorescein, fluorescein derivatives, or contrast agents for imaging purposes MRI or X-ray investigations, e.g., Gd-DTPA for MRI.

According to another aspect of the invention, the albumin-binding compounds of the invention confer better tissue penetration capacity upon the agent they are conjugated with. Herein, the expression "tissue penetration capacity" may refer to either the extent of tissue penetration by an agent on the one hand, or to the specificity or selectivity of tissue penetration by an agent on the other, or to both of these aspects of tissue penetration.

For the purposes of the present invention, tissue penetration is measured by quantification of a drug/agent in the desired tissue after different time points. This is preferably achieved by labelling the molecules (eg. radioactivity, fluorescence) prior to injection or by direct quantification by Liquid Chromatography/Mass Spectrometry/Mass Spectrometry (LC/MS/MS). Blood-half life and tissue-penetration are correlated as described for the case of antibodies and antibody fragments of different formats in reference 18, where it was shown that an increase of serum half-life is correlated with an increase of accumulation in the tumour.

The above aspects of the invention will be thus be advantageous when applied, e.g., to agents that may be targeted to their intended site of action using albumin as a vehicle. Thus, an anticancer drug may be efficiently targeted to rapidly growing tumours that utilise albumin as a nutrient.

An advantage arising from all of the above aspects of the invention is that the conjugation of the albumin-binding compounds of the invention to therapeutic or diagnostic agents may allow said agents to be administered to patients or subjects in lower doses. This advantage of the invention thus lowers the risk and/or severity of side effects, adverse reactions or complications of said agents.

When, for example, a diagnostic imaging agent such as a fluorophore or a contrast agent is conjugated to a compound of the invention, the resulting conjugate derivative of the agent, which is capable of non-covalent binding to albumin, is characterised by a slower blood clearance profile and allows higher signal intensity (e.g. a fluorescent, magnetic resonance, X-ray, positron emission tomography (PET) or single photon emission computed tomography (SPECT) signal) to be obtained, e.g. from blood vessels, compared to the non-derivatised agent, thus allowing the administration of lower doses and also yielding diagnostic images (e.g., an angiogram, an MRI image, and X-ray image or a PET) of better quality. This is particularly the case, e.g., for fluorescein and derivatives thereof, and their use in opthalmological angiography.

In view of their affinity, solubility and pharmacokinetic behaviour, the albumin-binding compounds of the invention are thus ideally suited, for example, to the coupling to contrast agents such as Gd-DTPA, thus extending half-lives and improving relaxation properties (preferably, shortened relaxation times compared to the contrast agent when not coupled to an albumin-binding compound of the invention).

A general advantage of the albumin-binding compounds of the invention is that they may be used, due to their relatively small size and good solubility, to confer albumin binding affinity upon small-molecule agents without substantially affecting the solubility or other pharmacologically relevant properties of said small-molecule agent.

A further advantage of the albumin-binding compounds of the invention is that they are universally portable, i.e., highly versatile. That is, said compounds may be conjugated to any agent, provided that the agent to be conjugated comprises a functional group that is capable of bonding to the albumin-binding compound, i.e., said functional group is capable of undergoing reaction such that the agent becomes bonded to the albumin-binding compound, or provided that such a functional group may be introduced into the agent. The use, according to the invention, of the compounds of the invention for such conjugation, leads to the conjugates of the invention, wherein the residue of an albumin-binding compound of the invention may be bonded either directly or indirectly, to the residue of an agent of interest.

The invention further provides medical, therapeutic and diagnostic uses of said conjugates.

DETAILED DISCLOSURE OF THE INVENTION

Compounds According to the Invention

The present invention provides a class of portable albumin-binding compounds represented by Formula 1

(Formula 1)

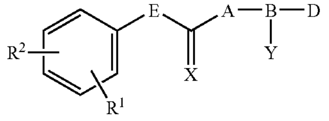

wherein E is a branched, unbranched or cyclic hydrocarbyl group of up to 6 carbon atoms optionally interrupted by up to 2 heteroatoms, optionally substituted by up to 6 groups selected from F, Cl, Br, I, branched, unbranched or cyclic $C_1$-$C_{10}$ hydrocarbyl groups, $OR^9$, $OCOR^9$, $COOR^9$, CHO, $COR^9$, $CH_2NR^9R^{10}$, $SR^9$, =O, =S and =NH;

X is O or S;

A is NH, O, S or $CR^9R^{10}$;

D is a functional group of up to 10 atoms, which is negatively charged or may be deprotonated to yield a negative charge;

$R^1$ and $R^2$ are independently selected from H, F, Cl, Br, I, branched, unbranched or cyclic $C_1$-$C_{10}$ hydrocarbyl groups, $OR^9$, $OCOR^9$, $COOR^9$, $CH_2OR^9$, CHO, $COR^9$, $NR^9R^{10}$ and $SR^9$; or $R^1$ and $R^2$ are joined to form a cyclic structure comprising a branched, unbranched or cyclic $C_1$-$C_{10}$ hydrocarbyl group (wherein said hydrocarbyl group is optionally interrupted by up to 2 heteroatoms and optionally substituted by up to 3 groups independently selected from F, Cl, Br, I, $OR^9$, $OCOR^9$, $COOR^9$, CHO, $COR^9$, $CH_2OR^9$, $NR^9R^{10}$, $CH_2NR^9R^{10}$, $SR^9$, =O, =S and =NH);

B comprises a branched, unbranched or cyclic hydrocarbyl group of up to 30 carbon atoms, optionally interrupted by up to 10 heteroatoms or a peptidyl chain of up to 20 amino acid residues, wherein B is optionally substituted with 1-5 groups selected from F, Cl, Br, I, =O, $OR^9$, $OCOR^9$, $COOR^9$, CN, $NR^9$, $NR^9R^{10}$, and $SR^9$, provided that B comprises at least 3 atoms in a chain between group D and the group A;

Y is a functional group capable of bonding to a therapeutic or diagnostic agent molecule;

and $R^9$ and $R^{10}$ are independently selected from the group H and branched, unbranched and cyclic $C_1$-$C_{10}$ hydrocarbyl groups, or a salt thereof.

The invention moreover provides albumin-binding conjugates, represented by Formula 2:

(Formula 2)

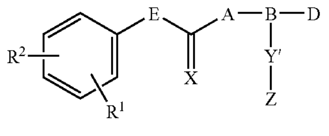

wherein E is a branched, unbranched or cyclic hydrocarbyl group of up to 6 carbon atoms optionally interrupted by up to 2 heteroatoms, optionally substituted by up to 6 groups selected from F, Cl, Br, I, branched, unbranched or cyclic $C_1$-$C_{10}$ hydrocarbyl groups, $OR^9$, $OCOR^9$, $COOR^9$, CHO, $COR^9$, $CH_2OR^9$, $NR^9R^{10}$, $CH_2NR^9R^{10}$, $SR^9$, =O, =S and =NH;

X is O or S;

A is NH, O, S or $CR^9R^{10}$;

D is a functional group of up to 10 atoms which is negatively charged or may be deprotonated to yield a negative charge;

$R^1$ and $R^2$ are independently selected from H, F, Cl, Br, I, branched, unbranched or cyclic $C_1$-$C_{10}$ hydrocarbyl groups, $OR^9$, $OCOR^9$, $COOR^9$, $CH_2OR^9$, CHO, $COR^9$, $NR^9R^{10}$ and $SR^9$; or $R^1$ and $R^2$ are joined to form a cyclic structure comprising a branched, unbranched or cyclic $C_1$-$C_{10}$ hydrocarbyl group (wherein said hydrocarbyl group is optionally interrupted by up to 2 heteroatoms and optionally substituted by up to 3 groups independently selected from F, Cl, Br, I, $OR^9$, $OCOR^9$, $COOR^9$, CHO, $COR^9$, $CH_2OR^9$, $NR^9R^{10}$, $CH_2NR^9R^{10}$, $SR^9$, =O, =S and NH);

B comprises a branched, unbranched or cyclic hydrocarbyl group of up to 30 carbon atoms, optionally interrupted by up to 10 heteroatoms or a peptidyl chain of up to 20 amino acid residues, wherein B is optionally substituted with 1-5 groups selected from F, Cl, Br, I, =O, $OR^9$, $OCOR^9$, $COOR^9$, CN, $NR^9$, $NR^9R^{10}$, =S, and $SR^9$, provided that B comprises at least 3 atoms in a chain between group D and the group A;

Y' is a residue of a functional group capable of bonding to a therapeutic or diagnostic agent molecule;

Z comprises the residue of a therapeutic or diagnostic agent molecule and optionally a linker.

and $R^9$ and $R^{10}$ are independently selected from the group H and branched, unbranched and cyclic $C_1$-$C_{10}$ hydrocarbyl groups, or a pharmaceutically acceptable salt thereof.

According to preferred embodiments, moiety E comprises a moiety represented by Formula 3:

(Formula 3)

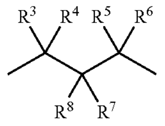

wherein $R^3$-$R^8$ are independently selected from H, F, Cl, Br, I, branched, unbranched or cyclic $C_1$-$C_{10}$ hydrocarbyl groups, $OR^9$, $OCOR^9$, $COOR^9$, CHO, $COR^9$, $CH_2OR^9$, $NR^9R^{10}$, $CH_2NR^9R^{10}$ and $SR^9$;

or the pairs of substituents $R^3$ and $R^4$ together, $R^5$ and $R^6$ together, or $R^7$ and $R^8$ together are optionally independently selected from the group =O, =S and NH.

In further preferred embodiments of the invention, moiety E comprises a moiety represented by Formula 4:

(Formula 4)

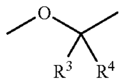

wherein $R^3$ and $R^4$ are independently selected from H, F, Cl, Br, I, branched, unbranched or cyclic $C_1$-$C_{10}$ hydrocarbyl groups, $OR^9$, $OCOR^9$, $COOR^9$, CHO, $COR^9$, $CH_2OR^9$, $NR^9R^{10}$, $CH_2NR^9R^{10}$ and $SR^9$;

or the pair of substituents $R^3$ and $R^4$ together is optionally independently selected from the group =O, =S and =NH.

The compounds and conjugates of the invention are capable of binding to albumin, that is, they have affinity for albumin. Their affinity of the compounds is preferably such that their dissociation constant is 100 μM or lower, more preferably 90, 80, 70, 60, 50, 40, 30, 20, 10, 9, 8, 7, 6, 5, 4, 3, 2, or 1 μM or lower, more preferably 90, 80, 70, 60, 50, 40, 30, 20, 10, 9, 8, 7, 6, 5, 4, 3, 2, or 1 nM or lower.

Preferably, the compounds and conjugates of the invention bind selectively to albumin. A albumin binder is said to have selective affinity for albumin with respect to an alternative binding partner if the albumin binder binds with higher affinity to albumin than to an alternative binding partner, wherein the dissociation constant for binding of said albumin binder to the alternative binding partner is at least 1.5-fold, preferably at least 2-, 3-, 5-, 10-, 15-, 20-, 25-, 30-, 35-, 40-, 45-, 50-, 60-, 70-, 80-, 90-, 100-200-, 300-, 400-, 500-, 750-, or 1000-fold the dissociation constant for binding of said albumin binder to albumin.

In one embodiment of the invention, moiety B together with group D comprises an amino acid residue. An amino acid is any organic molecule comprising both an acidic and an amino functional group. One or both of said groups may optionally be derivatised. The amino and the acidic group may be in any position relative to each other, but amino acids typically comprise 2-amino carboxylic acids, 3-amino carboxylic acids, 4-amino carboxylic acids, etc., i.e. in preferred embodiments, the amino group is on the atom numbered 2, 3, 4, 5, 6, 7, 8, 9, 10, 11, 12, 13, 14, 15, 16, 17, 18, 19, 20, etc., according to the IUPAC naming conventions [17, 19]. Following alternative naming conventions, which are also known to the person skilled in the art, said amino acid may be an α-, β-, γ-, δ-, ε-(etc.) up to an ω-amino acid. In a preferred embodiment, the amino acid may be an amino carboxylic acid [e.g., 17, 19]. However, in other embodiments, the acidic group on the amino acid is selected from the group $-OPO_3H$, $-PO_3H$, $-OSO_3H$ and $-SO_3H$. In preferred embodiments, said amino acid is a naturally occurring amino acid, or a derivative thereof. In further preferred embodiments, the amino acid is an alpha (α-) amino acid, wherein the amino acid may be a D- or an L-amino acid. Preferably the amino acid is the D- or the L-enantiomer of an amino acid selected from the group arginine, asparagine, aspartate, cysteine, glutamate, glutamine, glycine, histidine, leucine, lysine, methionine, phenylalanine, proline, serine, threonine, tryptophan, tyrosine and/or valine. Most preferably, said amino acid is D-lysine or L-lysine. In embodiments employing the D-enantiomer, the use of the D-enantiomer may provide the beneficial effect of further reducing the rate of metabolisation and thus clearance from the bloodstream.

In preferred embodiments, when B or B-D comprises an amino acid residue, Y may, as the skilled person would appreciate, conveniently be the amino group of the amino acid, most preferably the alpha (α-) amino group of an α-amino acid.

According to a further embodiment of the invention, B is cleavable under physiological conditions, preferably under conditions found in vivo at the desired site of action of a moiety derived from a therapeutic or diagnostic agent in a conjugate of the invention. Thus according to some embodiments, the conditions found at said site are pathophysiological conditions, though according to other embodiments, said conditions are the normal conditions found in a particular tissue or type of cell. Pathophysiological conditions are preferably conditions found in cancerous tissue, at a site of a tumour, at a site of inflammation, coagulation or pathological plaque formation (e.g. atherosclerotic or amyloid plaque formation), etc.

Said moiety B is preferably cleavable by hydrolysis, more preferably by the action of an enzyme, i.e., enzymatically. According to preferred embodiments said cleavage is by amidolysis or proteolysis, i.e. by action of a peptidase or a protease.

According to preferred embodiments of the invention, moiety B may thus be cleavable by an enzyme, i.e. B comprises a cleavage site that may serve as a substrate for an enzyme. Preferably, said enzyme is a hydrolytic enzyme, more preferably an amidolytic, peptidolytic or proteoteolytic enzyme (protease). Suitable enzymatic cleavage sites, in particular proteolytic cleavage sites, are well known to the person skilled in the art [21], and include sites for cleavage by enzymes such as metalloproteinases (matrix metalloproteinases, or pappalysins or adamalysins), serine proteases (e.g, thrombin, elastase, coagulation factors, plasmin, tissue plasminogen activator, urokinase or plasminogen activator), or cysteine proteases (such as cathepsins), carboxylic acid proteases, threonine proteases or glutamic acid proteases. Preferably, the cleavage site pertains to an enzyme selected from the group glucuronidase, urokinase-type-plasminogen activator, matrix metalloproteases, prostate specific antigen, human glandular kallikrein 2, plasmin, cathepsin B and PSMA.

According to certain embodiments of the invention, moiety B comprises a peptide. Said peptide preferably comprises of 2 or more amino acid residues, preferably of 3, 4, 5, 6, 7, 8, 9, 10, 11, 12, 13, 14, 15, 16, 17, 18, 19, 20. Most preferably, said peptide comprises a cleavage site [21] as described above, i.e., preferably a protease cleavage site, which is, moreover, preferably cleavable under particular pathophysiological conditions.

According to preferred embodiments of the invention, when moiety B of the compounds or conjugates of the invention does not contain a cleavable linker, the general class of compounds according to the invention may be further expanded by cleavable linkers, preferably linkers which are hydrolysable in vivo. Thus, in preferred embodiments, therapeutic or diagnostic agents may be coupled to the albumin-binding compounds of the invention using one or more amino acid linkers or peptides which may be cleaved by proteases, Schiff bases which may be hydrolyzed at 37° C. [20], cleavable esters or other chemical moieties which display a suitable compromise between sufficient stability in vitro and sufficiently rapid, and preferably selective, cleavability in vivo.

As mentioned above with reference to Formula 2, a linker may thus optionally be included within moiety Z, the linker preferably being cleavable, more preferably hydrolysable in vivo, most preferably selectively cleavable in vivo under defined conditions. The same applies to other formulae herein in which a moiety Z is defined.

The group D is preferably an acidic group or its conjugate base, and is more preferably selected from the group $OPO_3H$, $PO_3H$, $OSO_3H$, $SO_3H$ and COOH, preferably COOH, or the conjugate bases thereof (phosphate, phosphonate, sulfate, sulfonate and carboxylate), wherein the hydrogen atom H in the aforementioned formulae is replaced by a negative charge. Acidic groups are deprotonated to yield their conjugated bases in the presence of suitable proton acceptors (bases). The skilled person is aware of, and is able to predict, the circumstances under which such deprotonation occurs.

Hydrocarbyl groups or hydrocarbyl residues in the compounds and conjugates of the invention are the residues of hydrocarbon groups, that is, hydrocarbon chain radicals, preferably independently selected from the group alkyl, alkenyl, alkynyl, aryl and aralkyl.

As employed herein, the term "alkyl" comprises straight, branched and cyclic chain radicals having 1-30 carbon atoms, preferably 1-20, 1-15, 1-10, 1-8, 1-6, 1-4, 1-3 or 1-2 carbon atoms. Specific examples for alkyl residues are methyl, ethyl, propyl, isopropyl, butyl, pentyl, hexyl, octyl, decyl, undecyl, dodecyl, tridecyl, tetradecyl, pentadecyl, hexadecyl, heptadecyl, octadecyl, nonadecyl, icosyl, henicosyl, docosyl, tricosyl, tetracosyl, pentacosyl, hexacosyl, heptacosyl, octacosyl, nonacosyl or triacosyl, including the various branched-chain and/or cyclic isomers thereof, e.g. tert.-butyl or isopentyl, and so on.

As employed herein, the term "cyclic" includes the term "polycyclic", referring to structures having more than one ring structure. In particular, the term "cyclic" also refers to spirocyclic structures, wherein two or more rings have one atom in common, and fused polycyclic structures, wherein two or more rings have at least two atoms in common. A preferred embodiment of said fused polycyclic structure is adamantane or a residue thereof (the adamantyl radical).

The term "alkenyl" as employed herein comprises straight, branched and cyclic chain radicals having 2-30 carbon atoms, preferably 2-20, 2-15, 2-10, 2-8, 2-6, 2-4, or 2-3 carbon atoms, including at least one carbon-to-carbon double bond. Specific examples of "alkenyl" groups are the various alkenic unsaturated equivalents of those given with respect to alkyl groups, named after the conventions known to the person skilled in the art [17, 19], depending on the number and location of carbon-to-carbon double bond or bonds, e.g. butanediylidene, 1-propanyl-3-ylidene. "Alkenyl" groups preferably contain at least 1, more preferably at least 2, 3, 4, 6, 7, 8, 9, 10, 11, 12, 13, 14, 15, or 16 double bonds, wherein a double bond is preferably located at position 1, 2, 3, 4, 5, 6, 7, 8, 9, 10, 12, 13, 14, 15, 16, 17, 18, 19, 20, 21, 22, 23, 24, 25, 26, 27, 28 or 29 of the hydrocarbyl chain.

The term "alkynyl" as employed herein comprises straight, branched and cyclic chain radicals having 2-30 carbon atoms, preferably 2-20, 2-15, 2-10, 2-8, 2-6, 2-4, or 2-3 carbon atoms, including at least one carbon-to-carbon triple bond. Specific examples of "alkynyl" groups are the various alkynic unsaturated equivalents of those given with respect to alkyl and alkenyl groups, named after the conventions known to the person skilled in the art [17, 19], depending on the number and location of carbon-to-carbon triple bond or bonds. "Alkynyl" groups preferably contain at least 1, more preferably at least 2, 3, 4, 6, 7, 8, 9, 10, 11, 12, 13, 14, 15, or 16 triple bonds, wherein a double triple bond is preferably located at position 1, 2, 3, 4, 5, 6, 7, 8, 9, 10, 12, 13, 14, 15, 16, 17, 18, 19, 20, 21, 22, 23, 24, 25, 26, 27, 28 or 29 of the hydrocarbyl chain. The term "alkynyl" moreover includes "alkynyl" groups further comprising at least one carbon-to-carbon double bond, that is, "alkynyl" groups that fall under the definitions of both "alkynyl" and "alkenyl" groups as employed herein.

As employed herein, the term "aryl" refers to monocyclic or polycyclic or fused-polycyclic aromatic ring systems having 2-30, preferably 2-20, 2-10, more preferably 2-6 carbon atoms.

As employed herein, the term "aralkyl" refers to groups comprising at least one alkyl group and at least one aryl group as defined herein. In an aralkyl group as defined herein, the aralkyl group is bonded to another moiety of the compounds or conjugates of the invention via the alkyl group as exemplified by a benzyl group.

As used herein, the term "heteroatoms" includes N, O, S, P, preferably N and O.

In embodiments wherein $R^1$ and $R^2$ are joined in order to, together, form a cyclic structure, said cyclic structure is preferably a linear or branched hydrocarbyl chain of 3-10, more preferably, 3-9, 3-8, 3-7, 3-6, 3-5, 3-4 or 4 carbon atoms bonded at two positions to the phenyl ring of Formula 1 or Formula 2, i.e. forming two bonds to said phenyl ring, such as to form a ring structure fused to said phenyl ring. Preferably, said two bonds are preferably situated at the meta (3-) and para (4-) positions, at the ortho (2-) and meta positions or at the ortho and para positions of said phenyl ring. Said cyclic structure is optionally interrupted by up to 2, preferably 1 or none heteroatoms. Said cyclic structure is optionally substituted by up to 3, preferably up to 5, 4, 3, 2, 1 or none groups selected from F, Cl, Br, I, $OR^9$, $OCOR^9$, $COOR^9$, CHO, $COR^9$, $CH_2OR^9$, $NR^9R^{10}$, $CH_2NR^9R^{10}$, $SR^9$, =O, =S and =NH.

In a particularly preferred embodiment of the invention, said cyclic structure is a $C_4$ chain fragment (1,4-diradical) linked by its 1- and 4- atoms to said phenyl ring of Formula 1 or Formula 2 to form a six-membered ring fused to said phenyl ring, preferably at the meta and para positions of said phenyl ring, i.e., preferably forming a meta- and para-fused six-membered ring, as in the phenyl ring of compound 539 (FIG. 1), a compound that is useful for the synthesis of the compounds and conjugates of the invention.

According to preferred embodiments of the invention, $R^1$ and $R^2$ are independently selected from the group I, Br, $CH_3$, and H. More preferably, $R^1$ is in the para position and is selected from the group I, Br and $CH_3$, and $R^2$ is H.

In some preferred embodiments, $R^3$-$R^8$ are H. Independently thereof, of $R^9$ and $R^{10}$, may, in preferred embodiments, also be H.

(Formula 6)

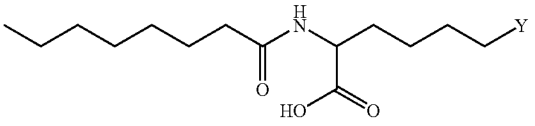

According to further preferred embodiments, the compounds of the invention are represented by Formula 7:

(Formula 7)

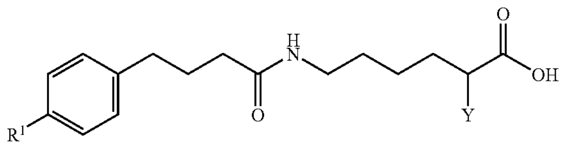

According to further preferred embodiments, the compounds of the invention are represented by Formula 8:

(Formula 8)

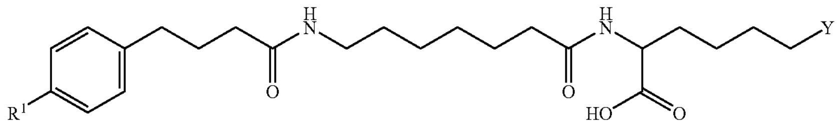

Any functional group, or plurality of functional groups, on a albumin-binding compound of the invention or on an agent to be linked thereto may be used for associating the compound and the agent, provided that the functional groups on said compound and said agent are capable of undergoing reaction such that the compound becomes linked to the compound. Preferably said linkage, i.e., conjugation, is by covalent bonding, though noncovalent bonding (e.g., hydrogen bonding, ionic bonding, van-der-Waals bonding) is also envisaged. In this specification, bonding, linking coupling or conjugation, of an agent to a compound means that said agent and compound or their residues are linked either directly or indirectly via a further molecular moiety.

According to preferred embodiments, Y is selected from the group —$NH_2$, —SH, —OH, —CHO, —NCS, —NCO and H. Preferably, Y is —$NH_2$. When Y is —$NH_2$, the compounds of the invention also comprise the protonated form (conjugated acid) thereof ($NH_3^+$).

In preferred embodiments of the compounds of the invention, B(Y)-D comprises a moiety represented by Formula 5:

(Formula 5)

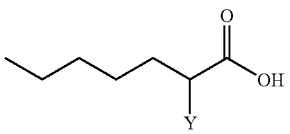

In other preferred embodiments of the compounds of the invention, B(Y)-D comprises a moiety represented by Formula 6:

According to preferred embodiments, B comprises a residue selected from the group 3-[2-aminylethyl)dithio]propionyl, N-[α-maleimido-3'-yl-acetyl, N,N'-1,4-bis-maleimido-3',3"-diyl-butane, N,N'-1,6-bis-maleimido-3',3"-diyl-hexane, N,N'-1,2-bis-maleimido-3',3"-diyl-ethane, N,N'-1,4-bis-maleimido-3',3"-diyl-2,3-dihydroxybutane, N-[β-maleimido-3'-yl-propionyl, N-[β-maleimido-3'-yl-semicarbazyl, N,N'-1,8-bis-maleimido-3',3'-diyl-triethyleneglycol, N,N'-1,1'-bis-maleimido-3',3'-diyl-tetraethyleneglycol, suberyl, dimethyladipimidyl, dimethylpimelimidyl, dimethylsuberimidyl, 1,4-di-[3'-(2'-thiyl)-propionamido]butane, glutaryl, dithiobispropionyl, tartaryl, dimethyl 3,3'-dithiobispropionimidyl, 3,4-dithio-N, N'-1,6-bis-maleimido-3',3"-diyl-hexane, ethylene glycol bis-succinyl, N-7-maleimido-3'-yl-caproyl, N-7-maleimido-3'-yl-caproylsemicarbazyl, N-[γ-maleimido-3'-yl-butyryl, 1,6-hexane-bis-vinylsulfone, N-[κ-maleimido-3'-yl-undecanoyl, N-[κ-maleimido-3'-yl-undecanoylsemicarbazyl, 4-[N-maleimido-3'yl-methyl]cyclohexane-1-carboxy-[6-amidocaproyl], 6-[3-mercapto-bropionamidohexanoyl, m-[maleimido-3-yl]-benzoyl, 4-(4-N-maleimido-3'-ylphenyl) butyrylsemicarbazyl, adipyl, 3-mercapto-propionylsemicarbazyl, N-[p-maleimido-3-ylphenyl]ureyl, 2-mercaptoacetyl, 3-mercaptopropionyl, 3[bromoacetamido]propionyl, 2-iodoacetyl, 4-[iodo acetyl]aminobenzoyl, 4-[N-maleimido-3'-ylmethyl]cyclohexane-1-carboxyl, 4-[p-maleimido-3'-yl]butyryl, 6-[β-maleimido-3-yl-propionamido]hexanoyl, and p-[2-mercaptoethyl]benzoyl, and 4-thiobutanimidamidyl.

According to preferred embodiments of the conjugates of the invention, Y' is selected from the group —NH—, —S—, —O—, —CO—, —NHCS—, —NHCO— and a bond. Preferably, said bond is a covalent bond. Most preferably, Y' is —NH—.

According to preferred embodiments of the conjugates of the invention, B(Y'-Z)-D comprises a moiety represented by Formula 9:

(Formula 9)

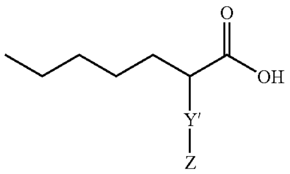

According to further preferred embodiments of the conjugates of the invention, B(Y'-Z)-D comprises a moiety represented by Formula 10:

(Formula 10)

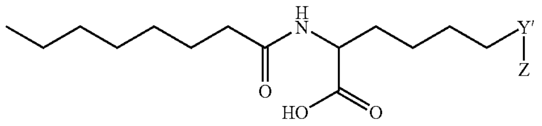

According to particularly preferred embodiments of the invention the conjugates of the invention comprise a moiety represented by Formula 11:

(Formula 11)

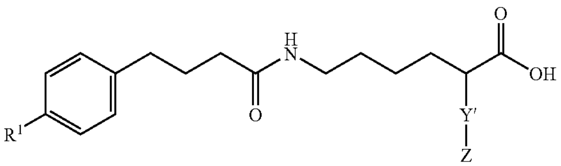

According to further preferred embodiments of the invention, the conjugates of the invention comprise a moiety represented by Formula 12:

(Formula 12)

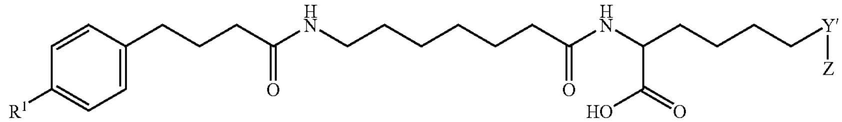

In further preferred embodiments, compounds or conjugates of the invention, the group

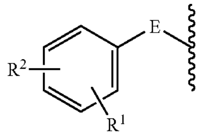

is selected from the group consisting of (Formula 13)

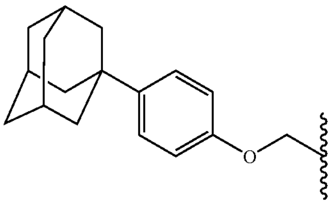

-continued (Formula 14)

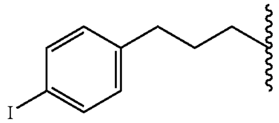

(Formula 15)

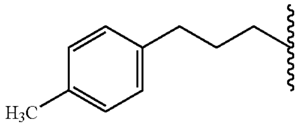

(Formula 16)

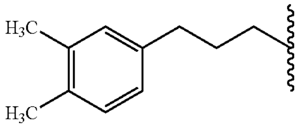

(Formula 17)

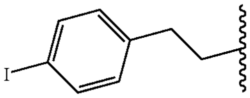

(Formula 18)

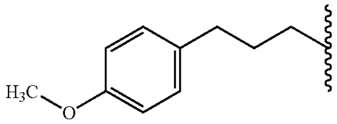

(Formula 19)

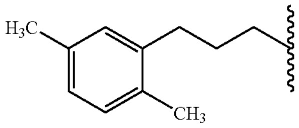

-continued (Formula 20)

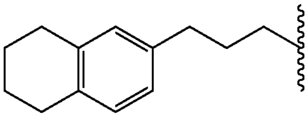

(Formula 21)

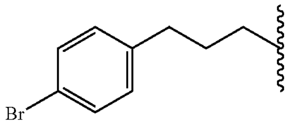

(Formula 22)

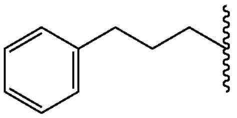

-continued (Formula 23)

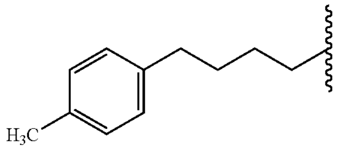

(Formula 24)

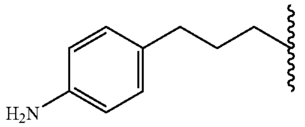

According to the invention, the therapeutic or diagnostic agent to be conjugated to the compounds of the invention, may be any type of agent. The term "diagnostic agents" includes imaging agents. Preferably, the compounds of the invention may be conjugated to an organic compound, a metalloorganic compound, a compound comprising a radionuclide, a nucleotide, a nucleic acid, a polymer, a peptide, a nucleopeptide, a protein, a lipid, a steroid, or a derivative or combination of any thereof. Preferably, said agent is selected from the group small molecules, peptides, antibodies, therapeutic proteins, antisense oligonucleotides, and inorganic or organic molecules or complexes comprising radionuclides.

According to the invention, said albumin binders may be used, due to their relatively small size and good solubility, for conjugation to small-molecule agent without substantially affecting, preferably without substantially reducing, the solubility or other pharmacologically relevant properties of the small-molecule agent. Preferably, the solubility of an agent conjugated to a compound according to the invention, is at least 1%, more preferably at least 5%, 10%, 20%, 30%, 40%, 50%, 60%, 70%, 80%, 90%, 95%, 98%, 99% or 100% of said agent when not conjugated.

Herein, the term "small molecules" refer to molecules, preferably organic molecules, with a molecular weight of less than about 1500 Da, in particular less than 1200, 1000, 900, 800, 700, 600, 500, 400, 350, 300, 250 or 200 Da.

Herein, the terms "protein", "peptide" or "polypeptide" are used interchangeably and refer to amino acid polymers of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labelling component. Also included within the definition are, for example, polypeptides containing one or more analogues of an amino acid (including, for example, unnatural amino acids, etc.), as well as other modifications known in the art. Polypeptides can occur as single chains or associated chains, and may of the invention can be naturally or non-naturally glycosylated (i.e. the polypeptide has a glycosylation pattern that differs from the glycosylation pattern found in the corresponding naturally occurring polypeptide).

According to preferred embodiments of the invention, the therapeutic agent molecule to which the compounds of the invention are conjugated, or the residue of which is comprised in a conjugate according to the invention, is a drug for treating cancer, a tumor, cardiovascular disease, obesity, viral, bacterial, fungal or other infections, inflammation, neurological disorders, degenerative neurological disorders, psychiatric diseases or conditions, depression, hormonal disorders, glucose metabolism disorders or diabetes, or a drug for contraception.

Herein, the terms "therapy", "treatment", "to treat" and "therapeutic", include the aspects of "prophylaxis", "prevention", "to prevent" and "prophylactic", respectively.

According to some embodiments, said therapeutic agent is a drug for treating a colorectal, breast, prostate, lung, head-and-neck, pancreatic, stomach or ovarian cancer, or a lymphoma, a leukemia, an astrocytoma, a high-grade astrocytoma, or a hepatocellular carcinoma. In one preferred embodiment, said agent is a drug for treating rapidly growing tumours (preferably, tumours with a doubling time of less than 120, 100, 80, or 60 days). Herein, the term "tumour doubling time" refers to the time in which the volume of the tumour doubles (tumour volume doubling time, see reference 22), as measured, e.g., in reference 23.

In a particularly preferred embodiment of the invention, said therapeutic agent molecule is a drug for the treatment of a tumour characterized by a rapid uptake of albumin.

When an albumin-binding compound of the invention and an agent are conjugated either directly or via a further linking moiety (linker), and either moiety B as defined herein or said linker is cleavable under certain conditions, preferably under pathophysiological conditions, the product of said cleavage reaction no longer retains affinity for albumin, or its affinity for albumin is reduced. According to specific embodiments of the invention, a conjugate according to the invention thus comprises an agent or drug which is capable of penetrating and/or tissues or cells after cleavage of said linker. According to this aspect of the invention, said conjugate may thus be a prodrug.

According to further preferred embodiments of the invention, the diagnostic agent molecule is an agent for diagnostic imaging techniques, fluorescence, angiography, fluoroangiography, ultrasonography, magnetic resonance-based diagnostic procedures, magnetic resonance imaging, X-ray imaging, nuclear medicine, single photon emission computed tomography (SPECT) or positron emission tomography (PET). In particularly preferred embodiments, said agent is a fluorophore for opthalmological angiography or a contrast agent for X-ray or magnetic resonance imaging. Most preferably, said agent comprises fluorescein or Gadolinium (III)—diethyltriaminepentaacetic acid (Gd-DTPA), or a residue thereof $^{177}$Lu—complexes of DTPA are equally preferred.

In preferred embodiments, the therapeutic or diagnostic agent is connected to moiety B via a thiourea moiety (as exemplified with the agent fluorescein in the compound "428-D-Lys-FITC"; see below, under "Synthesis of compounds" (2) and Example 6) or via an amide moiety (as exemplified with the agent fluorescein in the compound "428-D-Lys-FAM"; see below, under "Synthesis of compounds" (1) and Example 7).

Structures of examples of conjugates of the invention (428-Lys-FITC, 428-Lys-FAM, and 428-Lys-β-Ala-DTPA-Gd) are shown in FIG. 7.

Preparation of the Compounds and Conjugates of the Invention

The albumin-binding compounds and conjugates of the invention may be synthesised and coupled to drugs carrying suitable functional groups according to methods, e.g. methods of synthetic organic chemistry [24, in particular 25], that are well known to the According to preferred embodiments, the compounds of the invention are synthesised starting from carboxylic acid precursors exemplified by the preferred compounds shown in FIG. 1. Carboxylic acid precursors are commercially available (e.g., from SIGMA-ALDRICH, hereinafter referred to as SIGMA, The Sigma-Aldrich Library of Rare Chemicals, hereinafter referred to as SALOR, or Maybridge, or may be synthesised by methods known in the art [24]. The preferred carboxylic acid precursors shown in FIG. 1 are available from the following sources:

| Molecule No. (cf. FIG. 1) | Supplier | Catalogue Number |
|---|---|---|
| 326 | SALOR | R787981 |
| 428 | SIGMA | I5634 |
| 533 | SALOR | S532649 |
| 535 | SALOR | S714461 |
| 536 | SALOR | S347213 |
| 539 | SALOR | R244996 |
| 624 | Maybridge | MO01273CB |
| 622 | Fluka | 78250 |
| 625 | Trans World Chemicals | I 1232 |
| 630 | Biosynth | M 4301 |
| 631 | Fluka | 65170 |
| 632 | Aldrich | 330339 |

In embodiments wherein X is O and A is NH, a moiety B is preferably conjugated to the carboxylic acid of the carboxylic acid precursors component as described in Example 1 for compound 428 as the carboxylic acid precursor component and lysine, or 7-aminoheptanoic acid and lysine, as the components providing moiety B.

In embodiments wherein X is O and A is O, the carboxylic acid group of the carboxylic acid precursor component is preferably reacted with equimolar amounts of diethyl azodicarboxylate (DEAD), triphenylphosphane ($PPh_3$) and a component comprising moiety B and a hydroxyl (—OH) group. In embodiments wherein X is O and A is S the equivalent procedure is followed, except that the component comprising moiety B comprises a thiol (sulfhydryl, —SH) in place of the hydroxyl group.

In embodiments wherein X is O and A is CH, the carboxylic acid group of the carboxylic acid precursor component is preferably first converted to an acyl chloride by reaction with $SOCl_2$ and trace amounts of DMF; alternatively with $PPh_3$ in $CCl_4$. This is followed by addition of a ZnBr-derivative.

In embodiments wherein X is S, after the conjugation reactions described above for embodiments wherein X is O, the C═O group is transformed to a C═S using Lawesson's reagent.

Generally, functional groups (eg. $NH_2$, COOH, OH, SH etc) of the molecule providing moiety B, other than the group to be coupled to the carboxylic acid precursor component, are preferably protected (eg., the $NH_2$ using the Fmoc group, or COOH as a tert-butyl ester). Deprotection is preferably achieved before purification as described in Example 1 or by other methods known in the art.

According to certain preferred embodiments, for coupling of an albumin-binding compound to an agent, and in particular for the synthesis of moiety B when B comprises a peptide, and the skilled person may employ the well-known techniques of peptide chemistry [24-29].

In preferred embodiments wherein Y is $NH_2$, this primary amino group can be modified with a broad spectrum of reagents for the conjugation (coupling) to molecules of interest. In preferred examples, said $NH_2$ group of the albumin-binding moiety may be modified 1) by formation of an amide bond with, e.g., succinimide (NHS) esters, sulfo-NHS esters, acyl chlorides, acyl anhydrides, carboxylic acids after activation with 1-Ethyl-3-(3-dimethylaminopropyl)-carbodiimide (EDC)/NHS (or sulfo-NHS), HOBt (1-hydroxybenzotriazole), HBTU (O-(Benzotriazol-1-yl)-N,N,N',N'-tetramethyluronium hexafluorophosphate), HATU (O-(7-Azabenzotriazol-1-yl)-N,N,N',N'-tetramethyluronium hexafluorophosphate), TSTU (N,N,N',N'-Tetramethyl-O—(N-succinimidyl)uronium tetrafluoroborate) and others;
2) by formation of a urea/thiourea when reacted with isocyanates/isothiocyanates, and
3) by formation of a Schiff base with aldehydes.

In embodiments of the invention wherein bifunctional linkers are used to increase the range of chemical coupling groups for linking drugs to the albumin-binding moiety of the present invention, the introduction of 1) a maleimide by conjugation to an NHS-ester (e.g. 4-Maleimidobutyric acid N-hydroxysuccinimide ester, GMBS), or
2) a thiol group by Traut's reagent or a protected thiol are particularly preferred.

Alternatively, coupling of the albumin-binding compounds of the invention to small organic molecule drugs or protein drugs using the chemical modification of a thiol group (e.g., with maleimido or iodoacetamide) are preferred. In one embodiment of the invention, said thiol group is located on the agent to be coupled to an albumin-binding compound of the invention. In a further embodiment, Y is SH, and the thiol group may be located directly upon the albumin-binding compound of the invention. In a further embodiment, the SH group may be introduced into or added to the albumin-binding compound by means of a bifunctional linker as described above.

Specific procedures for the preparation of representative compounds of the invention are provided in Examples.

Albumin-binding moieties according to the invention may also be linked to drugs by non-covalent means, e.g. by base pairing using nucleotide, or modified nucleotide, moieties.

Pharmaceutical Compositions

The present invention provides the albumin-binding conjugates of the invention or pharmaceutically acceptable salts thereof, for use as a medicament. The invention also provides pharmaceutical compositions comprising said albumin-binding conjugates of the invention or pharmaceutically acceptable salts thereof, or the residues of the albumin-binding compounds of the invention bonded to a therapeutic or diagnostic agent or pharmaceutically acceptable salts thereof, and a pharmaceutically acceptable carrier.

The albumin-binding conjugates of the invention, or the albumin-binding compounds of the invention, are also provided for use in the preparation of a medicament, preferably for treating cancer, cardiovascular disease, obesity, viral, bacterial, fungal or other infections, inflammation, neurological disorders, degenerative neurological disorders, psychiatric diseases or conditions, depression, hormonal disorders, or for contraception.

The preparation of pharmaceutical compositions is well known to the person skilled in the art. Pharmaceutically acceptable salts of the albumin-binding conjugates of the invention can be prepared by conventional procedures, such as by reacting the free base and/or acid of an albumin-binding conjugate with at least a stoichiometric amount of the desired salt-forming acid or base, respectively.

Pharmaceutically acceptable salts of the albumin-binding conjugates of the invention include salts with inorganic cations such as sodium, potassium, calcium, magnesium, zinc, and ammonium, and salts with organic bases. Suitable organic bases include N-methyl-D-glucamine, arginine, benzathine, diolamine, olamine, procaine and tromethamine. Pharmaceutically acceptable salts according to the invention also include salts derived from organic or inorganic acids. Suitable anions include acetate, adipate, besylate, bromide, camsylate, chloride, citrate, edisylate, estolate, fumarate, gluceptate, gluconate, glucuronate, hippurate, hyclate, hydrobromide, hydrochloride. iodide, isethionate, lactate, lactobionate, maleate, mesylate, methylbromide, methylsulfate, napsylate, nitrate, oleate, pamoate, phosphate, polygalacturonate, stearate, succinate, sulfate, sulfosalicylate, tannate, tartrate, terephthalate, tosylate and triethiodide.

Pharmaceutical dosage forms of the albumin-binding conjugates of the invention may be provided in an instant release, controlled release, sustained release, or target drug-delivery system, notwithstanding that the pharmacokinetic properties of the drug contained in the pharmaceutical compositions of the invention are also influenced due to the presence of an albumin-binding moiety of the invention, i.e. the residue of an albumin-binding compound according to the invention that is comprised within an albumin-binding conjugate of the invention.

Commonly used dosage forms include, for example, ovules, implants, patches, liposomes, tablets, dragees, logenzes, soft or hard shell capsules, amorphous or crystalline powders, effervescent powders or tablets, aerosols, lyophilized formulations, solutions and suspensions, (micro-) emulsions, ointments, gels, creams, pastes, foams, suppositories. Depending on the route of administration used, special devices may be required for application or administration of the agent, such as, for example, syringes and needles, inhalers, pumps, injection pens, applicators, special flasks, or other devices for administration, which may also be implanted within the body.

Pharmaceutical dosage forms are often composed of the drug, an excipient(s), and a container/closure system. One or multiple excipients, also referred to as inactive ingredients, can be added to an albumin binder of the invention to improve or facilitate manufacturing, stability, administration, and safety of the drug, and can provide a means to achieve a desired drug release profile. Therefore, the type of excipient(s) to be added to the composition can depend on various factors, such as, for example, the physical and chemical properties of the agent and/or the albumin-binding moiety, the route of administration, and the manufacturing procedure. Pharmaceutically acceptable excipients are available in the art, and include those listed in various pharmacopoeias (see, e.g., [30,31]).

Pharmaceutical dosage forms of an albumin binder of the present invention may be manufactured by any of the methods well-known in the art, such as, for example, by conventional mixing, sieving, dissolving, melting, granulating, dragee-making, tabletting, suspending, extruding, spray-drying, levigating, emulsifying, (nano/micro-) encapsulating, entrapping, or lyophilization processes. As noted above, the compositions of the present invention can include one or more physiologically acceptable inactive ingredients that facilitate processing of active molecules into preparations for pharmaceutical use.

Proper formulation is dependent upon the desired route of administration. For intravenous injection, for example, the composition may be formulated in aqueous solution, if necessary using physiologically compatible buffers, including, for example, phosphate, histidine, or citrate for adjustment of the formulation pH, and a tonicity agent, such as, for example, sodium chloride or dextrose. For transmucosal or nasal administration, semisolid, liquid formulations, or patches may be preferred, possibly containing penetration enhancers. Such penetrants are generally known in the art. For oral administration, the albumin-binding conjugates can be formulated in liquid or solid dosage forms and as instant or controlled/sustained release formulations. Suitable dosage forms for oral ingestion by a subject include tablets, pills, dragees, hard and soft shell capsules, liquids, gels, syrups, slurries, suspensions, and emulsions. The pharmaceutical compositions according to the invention may also be formulated as rectal or vaginal dosage forms, such as suppositories or retention enemas, e.g., containing conventional suppository bases known to the skilled person, such as cocoa butter, glycerides, glycerinated gelatin, depolarized gelatin, polyethylene glycol, polysorbate, or others.

For oral administration, the albumin-binding conjugates of the invention will generally be provided in solid dosage forms, e.g., in the form of tablets or capsules, or as an aqueous solution or suspension.

Solid oral dosage forms can be obtained using excipients, which may include inert diluents, fillers, disintegrants, binders (dry and wet), dissolution retardants, lubricants, glidants, antiadherants, cationic exchange resins, wetting agents, antioxidants, preservatives, colouring, sweetening and flavouring agents. These excipients can be of synthetic or natural source. Examples of such excipients include cellulose derivatives, citric acid, dicalcium phosphate, gelatine, magnesium carbonate, magnesium/sodium lauryl sulfate, mannitol, polyethylene glycol, polyvinyl pyrrolidone, silicates, silicium dioxide, sodium benzoate, sorbitol, starches, stearic acid or a salt thereof, sugars (i.e. dextrose, sucrose, lactose, etc.), talc, tragacanth mucilage, vegetable oils (hydrogenated), and waxes. Ethanol and water may serve as granulation aides. In certain instances, coating of tablets with, for example, a taste-masking film, a stomach acid resistant film, or a release-retarding film is desirable. Natural and synthetic polymers, in combination with colorants, sugars, and organic solvents or water, are often used to coat tablets, resulting in dragees. When a capsule is preferred over a tablet, the drug powder, suspension, or solution thereof can be delivered in a compatible hard or soft shell capsule.

Suitable inert diluents include sodium and calcium carbonate, sodium and calcium phosphate and lactose. Corn starch and alginic acid are suitable disintegrating agents. Binding agents may include starch and gelatine. The lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral use include hard gelatine capsules in which the active ingredient is mixed with a solid diluent and soft gelatine capsules wherein the active ingredient is mixed with water or an oil such as peanut oil, liquid paraffin or olive oil.

For topical administration, via the skin or mucous membrane, the albumin binders may be formulated in a skin patch, as a semi-solid or a liquid formulation, for example a gel, a (micro-) emulsion, an ointment, a solution, a (nano/micro)-suspension, or a foam. The penetration of the albumin binders into the skin or mucous membrane and underlying tissues can be regulated, for example, using penetration enhancers; the appropriate choice and combination of lipophilic, hydrophilic, and amphiphilic excipients, including water, organic solvents, waxes, oils, synthetic and natural polymers, surfactants, emulsifiers; by pH adjustment; and use of complexing agents. Other techniques, such as iontophoresis, may be used to regulate skin penetration of an albumin binder of the invention. Transdermal or topical administration would be preferred, for example, in situations in which local delivery with minimal systemic exposure is desired.

For administration by inhalation, or administration to the nose, the albumin binders for use according to the present invention are conveniently delivered in the form of a solution, suspension, emulsion, or semisolid aerosol from pressurized packs, or a nebuliser, usually with the use of a propellant, e.g., halogenated carbons derived from methane and ethane, carbon dioxide, or any other suitable gas. For topical aerosols, hydrocarbons like butane, isobutene, and pentane are useful. In the case of a pressurized aerosol, the appropriate dosage unit may be determined by providing a valve to deliver a metered amount. Capsules and cartridges of, for example, gelatin, for use in an inhaler or insufflator, may be formulated. These typically contain a powder mix of the albumin binder and a suitable powder base such as lactose or starch.

Compositions formulated for parenteral administration by injection are usually sterile and, can be presented in unit dosage forms, e.g., in ampoules, syringes, injection pens, or in multi-dose containers, the latter usually containing a preservative. The compositions may take such foams as suspensions, solutions, or emulsions in oily or aqueous vehicles, and may contain formulatory agents, such as buffers, tonicity agents, viscosity enhancing agents, surfactants, suspending and dispersing agents, antioxidants, biocompatible polymers, chelating agents, and preservatives. Depending on the injection site, the vehicle may contain water, a synthetic or vegetable oil, and/or organic co-solvents. In certain instances, such as with a lyophilized product or a concentrate, the parenteral formulation would be reconstituted or diluted prior to administration. Depot formulations, providing controlled or sustained release of an agent of the invention, may include injectable suspensions of nano/micro particles or nano/micro or non-micronized crystals. Independently of the increase in the blood circulation time achieved by the albumin-binding moiety according to the invention, polymers such as poly (lactic acid), poly(glycolic acid), or copolymers thereof, can serve as controlled/sustained release matrices, in addition to others known in the art. Other depot delivery systems may be presented in form of implants and pumps requiring incision.

Suitable carriers for intravenous injection for the molecules of the invention are well-known in the art and include water-based solutions containing a base, such as, for example, sodium hydroxide, to form an ionized agent, sucrose or sodium chloride as a tonicity agent, for example. The water-based solution may comprise a buffer containing phosphate or histidine. Co-solvents, such as, for example, polyethylene glycols, may be added. These water-based systems are effective at dissolving agents of the invention and produce low toxicity upon systemic administration. The proportions of the components of a solution system may be varied considerably, without destroying solubility and toxicity characteristics. Furthermore, the identity of the components may be varied. For example, low-toxicity surfactants, such as polysorbates or poloxamers, may be used, as can polyethylene glycol or other co-solvents, biocompatible polymers such as polyvinyl pyrrolidone may be added, and other sugars and polyols may substitute for dextrose.

Uses of the Portable Albumin Binders/Methods of Treatment

The present invention provides the use of the albumin-binding compounds of the invention for binding a therapeutic or diagnostic agent molecule to albumin, i.e., for conferring upon said agent an affinity for albumin, or for increasing the affinity of said agent for albumin. Preferably the affinity of said agent is increased by a factor of at least 1.5, more preferably by a factor of at least 2, 3, 4, 5, 6, 7, 8, 9, 10, 20, 30, 40, 50, 60, 70, 80, 90, 100, 150, 200, 250, 300, 400, 500; 600, 700, 800, 900, 1000, 1500, 2000, 2500, 3000, 3500, 4000, 5000, 7000, $10^4$, $10^5$, $10^6$, $10^8$ or $10^9$.

The invention thereby provides the use of said compounds for decreasing the rate at which said agent is metabolised or degraded in the body of a subject, and thereby for increasing the blood circulation time (also referred to as the blood clearance time, the "blood clearance", or expressed in terms of the physiological half-life) of a therapeutic or diagnostic agent molecule. Moreover, the invention thus provides the use of said compounds for increasing the retention time of said agent in the vascular space. Preferably, said blood circulation time or said retention time of the agent in the vascular space is increased by a factor of at least 1.5, more preferably by a factor of at least 2, 3, 4, 5, 6, 7, 8, 9, 10, 20, 30, 40, 50, 60, 70, 80, 90, 100, 150, 200, 250, 300, 400, 500, 600, 700, 800, 900, 1000, 1500, 2000, 2500, 3000, 3500, 4000, 5000, 7000, $10^4$, $10^5$, $10^6$, or $10^7$.

Moreover, the invention provides the use of said compounds to improve the tissue penetration capacity of a therapeutic or diagnostic agent molecule. An improvement of tissue penetration capacity means that the use of a conjugate of the present invention leads to a greater accumulation of said conjugate and/or the therapeutic or diagnostic agent comprised therein or released therefrom after cleavage of a linker moiety) in a particular tissue or at a particular site of action, than would be achieved for said therapeutic or diagnostic agent alone, i.e. without conjugation to an albumin-binding compound according to the present invention. Preferably, said tissue penetration is increased by a factor of at least 1.5, more preferably by a factor of at least 2, 3, 4, 5, 6, 7, 8, 9, 10, 20, 30, 40, 50, 60, 70, 80, 90, 100, 150, 200, 250, 300, 400, 500, 600, 700, 800, 900, 1000, 1500, 2000, 2500, 3000, 3500, 4000, 5000, 7000, $10^4$, $10^5$, $10^6$, or $10^7$.

The invention moreover provides a method of treating a disease or condition is thus provided, comprising administering to a patient in need of such treatment an effective dose of an albumin-binding conjugate according to the invention, or an albumin-binding compound of the invention bonded to a therapeutic or diagnostic agent. In preferred embodiments, said disease or condition is cancer, cardiovascular disease, obesity, viral, bacterial, fungal or other infections, inflammation, neurological disorders, degenerative neurological disorders, psychiatric disease or condition, depression, or a hormonal disorder.

According to one preferred embodiment of the invention, said method comprises targeting said agent, by virtue of conjugation to an albumin-binding compound of the invention, to a tissue or site of action. Said site preferably comprises cancerous cells, a tumour, a site of inflammation, coagulation or pathological plaque formation (e.g. atherosclerotic or amyloid plaque formation), or any other sites having physiological or pathological characteristics that may be treated, visualised, or diagnosed by means of said agent.

According to a preferred embodiment, said tissue is characterised by a high rate of albumin uptake. Preferably, said tissue is a tumour, more preferably colorectal, breast, prostate, lung, head-and-neck, pancreatic, stomach or ovarian cancer, or a lymphoma, a leukemia, an astrocytoma, a high-grade astrocytoma, or a hepatocellular carcinoma. In one preferred embodiment, said tissue is a rapidly growing tumour (preferably, a tumour with a doubling time of less than 120, 100, 80 or 60 days).

According to further preferred embodiments, said method comprises the steps of binding a therapeutic or diagnostic agent to albumin by an albumin-binding moiety, i.e. an albumin-binding compound of the invention or the residue thereof, thereby delivering said agent to a desired site of action for said agent, or to a specific tissue, in a patient, using serum albumin as a carrier. In preferred embodiments, the agent is liberated from the albumin at said site of action or in said tissue. Moreover, said liberation of the agent is preferably achieved by chemical processing, preferably by cleavage of a cleavable linker connecting the agent and the albumin-binding moiety according to the invention, wherein said cleavage is preferably proteolytic cleavage. According to one embodiment, the agent is taken up by a tumour cell prior to said chemical processing.

In some embodiments of the methods of the invention, an agent to which an albumin-binding compound of the invention is conjugated blocks extracellular targets (e.g., receptors, cytokines, growth factors, and blood enzymes).

According to a further aspect of the invention, the invention provides the use of the compounds or conjugates for medical imaging purposes. The expression "medical imaging" comprises "diagnostic imaging" or "imaging diagnostics". Such a use according to the invention preferably comprises the modification of a therapeutic or diagnostic agent by conjugation with a compound of the invention to form a conjugate of the invention. Preferably, the agent to which the compound of the invention is conjugated is a diagnostic agent. The use of compounds and conjugates according to the invention for medical imaging purposes moreover preferably comprises administering to a patient an effective dose of a conjugate of the invention. As described elsewhere in this specification, said medical imaging is preferably a fluorescence-based method, angiography, fluoroangiography, ultrasonography, a magnetic resonance-based diagnostic procedure, magnetic resonance imaging, X-ray imaging, medicine, single photon emission computed tomography (SPECT) or positron emission tomography (PET).

Modes of Administration

The albumin-binding conjugates of the invention can be delivered directly or in pharmaceutical compositions containing excipients (see above), as is well known in the art. The present methods of treatment involve administration of a therapeutically effective amount of an albumin-binding compound of the invention to a subject.

The term "therapeutically effective amount" as used herein refers to an amount of a conjugate according to the present invention needed to treat, ameliorate, or prevent the targeted disease condition, or to exhibit a detectable therapeutic or preventative effect. In general, the therapeutically effective dose can be estimated initially either in cell culture assays or in animal models, for example, in non-human primates, mice, rabbits, dogs, or pigs. The animal model may also be used to determine the appropriate concentration range and route of administration. Such information can then be used to determine useful doses and routes for administration in humans.

The precise effective amount for a human subject will depend upon the severity of the disease state, general health of the subject, age, weight, and gender of the subject, diet, time and frequency of administration, drug combination(s), reaction sensitivities, and tolerance/response to therapy. This amount can be determined by routine experimentation and is within the judgement of the clinician. Generally, an effective amount, i.e., dose, of an agent, will be from 0.005 mg/kg to 50 mg/kg, preferably 0.125 mg/kg to 20 mg/kg.

Effective treatment regimes for preferred agents of the invention include administration one, two or three times daily, and/or one, two, three, four, five or six times weekly. These regimes are therefore particularly preferred for use in the present invention.

An effective and convenient route of administration and an appropriate formulation of the agents of the invention in pharmaceutical compositions (see above) may also be readily determined by routine experimentation. Various formulations and drug delivery systems are available in the art (see, e.g., [32, 33]).

Suitable routes of administration may, for example, include oral, nasal (intranasal), pulmonary or other mucosal, topical, transdermal, vaginal, rectal, intestinal, ocular, aural, parenteral administration.

Primary routes for parenteral administration include intravenous, intramuscular, and subcutaneous administration. Secondary routes of administration include intraperitoneal, intra-arterial, intra-articular, intracardiac, intracisternal, intradermal, intralesional, intraocular, intrapleural, intrathecal, intrauterine, and intraventricular administration. The indication to be treated, along with the physical, chemical, and biological properties of the drug, dictate the type of formulation and the route of administration to be used, as well as whether local or systemic delivery would be preferred.

For compositions useful for the present methods of treatment, a therapeutically effective dose can be estimated initially using a variety of techniques well-known in the art. Initial doses used in animal studies may be based on effective concentrations established in cell culture assays. Dosage ranges appropriate for human subjects can be determined, for example, using data obtained from animal studies and cell culture assays.

A therapeutically effective dose or amount of a conjugate, or a medicament or a pharmaceutical composition containing said conjugate, according to the present invention refers to an amount or dose of the conjugate, medicament or pharmaceutical composition that results in amelioration of symptoms or a prolongation of survival in a subject. Toxicity and therapeutic efficacy of such conjugate, medicament or pharmaceutical composition can be determined by standard pharmaceutical procedures in cell cultures or experimental animals, e.g., by determining the LD50 (the dose lethal to 50% of the population) and the ED50 (the dose therapeutically effective in 50% of the population). The dose ratio of toxic to therapeutic effects is the therapeutic index, which can be expressed as the ratio LD50/EDS). Conjugates, medicaments or pharmaceutical compositions that exhibit high therapeutic indices are preferred.

The effective amount or therapeutically effective amount is the amount of the conjugate, medicament or pharmaceutical composition that will elicit the biological or medical response of a tissue, system, animal, or human that is being sought by the researcher, veterinarian, medical doctor, or other clinician, e.g., control of tumour growth, control of infections, regulation of glucose metabolism, decrease in elevated or increased blood glucose levels, treatment or prevention of a disorder associated with altered glucose metabolism, e.g., diabetes, etc Dosages preferably fall within a range of circulating concentrations that includes the ED50 with little or no toxicity. Dosages may vary within this range depending upon the dosage form employed and/or the route of administration utilised. The exact formulation, route of administration, dosage, and dosage interval should be chosen according to methods known in the art, in view of the specifics of a subject's condition.

Dosage amount and interval may be adjusted individually to provide plasma levels of the active moiety that are sufficient to achieve the desired effects, i.e., minimal effective concentration (MEC). The MEC will vary for each agent but can be estimated from, for example, in vitro data and animal experiments. Dosages necessary to achieve the MEC will depend on individual characteristics and route of administration. In cases of local administration or selective uptake, the effective local concentration of the drug may not be related to plasma concentration.

The amount of agent or composition administered may be dependent on a variety of factors, including the sex, age, and weight of the subject being treated, the severity of the affliction, the manner of administration, and the judgement of the prescribing physician.

The present compositions may, if desired, be presented in a pack or dispenser device containing one or more unit dosage forms containing the active ingredient. Such a pack or device may, for example, comprise metal or plastic foil, such as a blister pack, or glass and rubber stoppers such as in vials. The pack or dispenser device may be accompanied by instructions for administration. Compositions comprising an agent of the invention formulated in a compatible pharmaceutical carrier may also be prepared, placed in an appropriate container, and labelled for treatment of an indicated condition.

BRIEF DESCRIPTION OF THE DRAWINGS

FIG. 12 summarises competition experiments to characterise binding of 428-D-Lys-FAM to HSA.

EXAMPLES

Example 1

Preparation of Compounds of the Invention ("428-Aminoheptanoic Acid-α-Lys-ϵ-$NH_2$" and "428-ϵ-Lys-α-$NH_2$")

Figure 1:
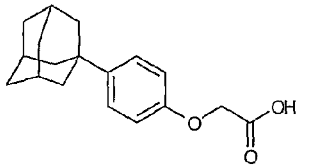
FIG. 1 shows the building-block reagents 326, 428, 533, 535, 536, 539, 622, 624, 625, 630, 631 and 632, starting from which the compounds of the invention may be synthesised.
Figure 1:
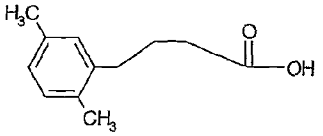
Figure 1:
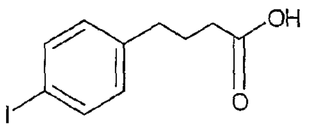
Figure 1:
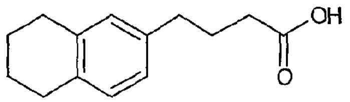
Figure 1:
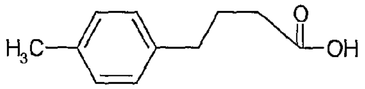
Figure 1:
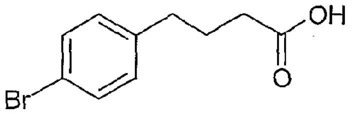
Figure 1:
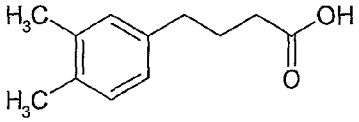
Figure 1:
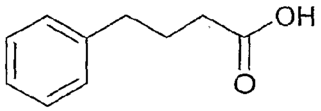
Figure 1:
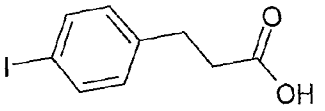
Figure 1:
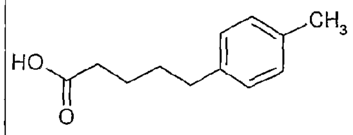
Figure 1:
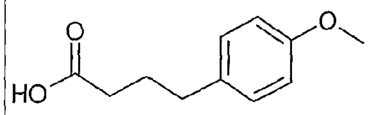
Figure 1:
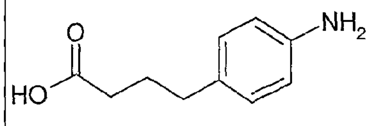

FIG. 1 shows possible building-block reagents, starting from which the compounds of the inventions may be synthesised. The carboxylic acid of compound 428 (obtainable from SIGMA, catalogue number I5634) was activated with one equivalent of EDC and 1.2 equivalents of NHS in DMSO for 4 h at 30° C. prior to addition of ten equivalents of 7-aminoheptanoic acid and triethylamine. The reaction was stirred overnight at 30° C., to yield 428-aminoheptanoic acid. The product was purified by HPLC (see Example 21, General Methods) and analysed by mass-spectrometry.

Generally, all molecules synthesized in the following examples were characterized by mass spectrometry.

In one preparation, 428-aminoheptanoic acid: 10 μmol of 428 were stirred with 8 μmol of N-(3-dimethylaminopropyl)-N'-ethylcarbodiimide (EDC) and 10 μmol of N-hydroxysuccinimide (NHS) in 50 μl of DMSO for 3 hours at 30° C. followed by addition of 20 μmol of 7-aminoheptanoic acid (Bachem) in 100 μl of 1 M $NaHCO_3$, pH 9. The reaction was allowed to stir overnight at 30° C. After quenching of remaining reagents with excess of Trizma base the reaction was purified by HPLC and characterized by mass spectrometry.

Figure 2:
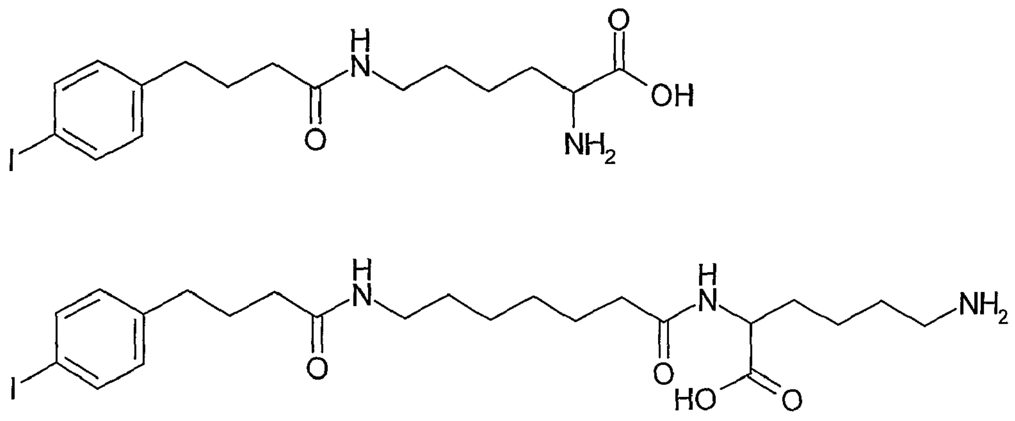
FIG. 2 shows structures of examples of preferred compounds of the invention, the extended albumin binding molecules 428-ϵ-Lys-α-$NH_2$ (top) and 428-aminoheptanoic acid-ϵ-Lys-α-$NH_2$ (bottom).

To obtain a "chemical handle" for use, according to the invention, in conjugation reactions with diverse agents, while retaining the presence of a carboxylic acid functionality which was required for albumin binding, a primary amino group was introduced by conjugation of Fmoc-D-Lys-OH via the ϵ-amino group to the carboxyl function of 428, or by conjugation of D-Lys(Fmoc)-OH via the α-amino group to the free carboxyl function of 428-aminoheptanoic acid (see FIG. 2). The synthesis and purification was performed as described above including a deprotection step after conjugation by addition of a large excess of triethylamine for 4 h prior to purification.

Example 2

Preparation of Compounds of the Invention ("533-Aminoheptanoic Acid-α-Lys-ϵ-$NH_2$" and "533-ϵ-Lys-α-$NH_2$")

The carboxylic acid of compound 533 (obtainable from SALOR, catalogue number S532649) is activated with one equivalent of EDC and 1.2 equivalents of NHS in DMSO for 4 h at 30° C. prior to addition of ten equivalents of 7-aminoheptanoic acid and triethylamine. The reaction is stirred overnight at 30° C., to yield 533-aminoheptanoic acid. The product is purified by HPLC and analysed by mass-spectrometry.

A primary amino group is introduced by conjugation of Fmoc-D-Lys-OH via the s-amino group to the carboxyl function of 533 or by conjugation of D-Lys(Fmoc)-OH via the α-amino group to the free carboxyl function of 533-aminoheptanoic acid. The synthesis and purification is performed as described above including a deprotection step after conjugation by addition of a large excess of triethylamine for 4 h prior to purification.

Example 3

Preparation of Compounds of the Invention ("539-Aminoheptanoic acid-α-Lys-ϵ-$NH_2$" and "539-6-Lys-α-$NH_2$")

The carboxylic acid of compound 539 ((obtainable from SALOR, catalogue number R244996) is activated with one equivalent of EDC and 1.2 equivalents of NHS in DMSO for 4 h at 30° C. prior to addition of ten equivalents of 7-aminoheptanoic acid and triethylamine. The reaction is stirred overnight at 30° C., to yield 539-aminoheptanoic acid. The product is purified by HPLC and analysed by mass-spectrometry.

A primary amino group is introduced by conjugation of Fmoc-D-Lys-OH via the ϵ-amino group to the carboxyl function of 539 or by conjugation of D-Lys(Fmoc)-OH via the α-amino group to the free carboxyl function of 539-aminoheptanoic acid. The synthesis and purification is performed as described above including a deprotection step after conjugation by addition of a large excess of triethylamine for 4 h prior to purification.

Example 4

Preparation of Compounds X-D-Lys (X=326, 428, 533, 535, 536, 539, 622 and 624)

In one set of experiments, molecules of the general formula X-D-Lys were also synthesised for various compounds "X" as follows (X=326, 428, 533, 535, 536, 539, 622 and 624): Activation of the carboxylic acid of moiety X was performed as described above in the Examples above. After addition of 20 μmol of Fmoc-D-Lys (Bachem) and 43 μmol of triethylamine (TEA) in 100 μl DMSO the reaction was stirred overnight at 30° C. Removal of the Fmoc-protection group at the α-amino position was performed by addition of 10 μl of 5 M KOH and stirring for 2 hours at 30° C. After purification by HPLC on a 0.1% trifluoroacetic acid gradient, the dried fractions containing X-D-Lys were resuspended in DMSO. 5 M HCl was added until the solution became clear.

Example 5

Modification of the "Chemical Handle" on the Compounds of the Invention

The conjugation of acetic or butanoic acid to the amino groups of 428-ϵ-Lys-α-$NH_2$ and 428-aminoheptanoic acid-α-Lys-ϵ-$NH_2$ respectively was achieved by activating the carboxylic acid with equimolar of EDC/NHS for 3 hours at 30° C. and subsequently adding the activated acid at 100× molar excess to 428-8-Lys-α-$NH_2$ and 428-aminoheptanoic acid-α-Lys-ϵ-$NH_2$ respectively and stirred for 12 hours at 30° C. Alternatively acetic anhydride was added at 100× molar excess to 428-ϵ-Lys-α-$NH_2$ and 428-aminoheptanoic acid-α-Lys-ϵ-$NH_2$ respectively and stirred for 12 hours at 30° C.

In one set of preparations, molecules of the general formula X-D-Lys-Ac (X=326, 428, 533, 535, 536, 539, and 624) were synthesised from X-D-Lys (prepared as described in Example 4 and resuspended in DMSO). In these cases, X-D-Lys was reacted with 10× molar excess of $Ac_2O$ for 4 hours at 30° C. after concentration determination by HPLC/UV. The product was purified by HPLC.

Example 6

Preparation of Conjugates of the Invention: Coupling to a Fluorophore (FITC/Thiourea Derivative)

The α-Amino Group of 428-ϵ-Lys-α-$NH_2$ was Conjugated to the Fluorescein-isothiocyanate (FITC), as an example of a fluorophore, diagnostic agent and, in general terms, drug-like molecule. Coupling was achieved by stirring 2.5 μmol of 428-6-Lys-α-$NH_2$ and 10 μmol of FITC for 12 h at 30° C. in 650 mM $NaH_2PO_4$, 30% DMSO, pH 7.2. The product (428-D-Lys-FITC) was purified by HPLC and characterized by mass-spectrometry.

Example 7

Preparation of Conjugates of the Invention: Coupling to a Fluorophore (FAM/Amide Derivative)

Amide Conjugates of 428-D-Lys, 622-D-Lys and, for Comparison, Phenethylamine to fluorescein (428-D-Lys-FAM, 622-D-Lys-FAM and phenethylamine-FAM) were prepared as follows: 19 μmol of phenethylamine, 428-D-Lys, or 622-D-Lys prepared as above and 14 μmol of 5-carboxyfluorescein NHS ester were dissolved in 120 μl DMSO. 72 μmol of TEA were added. The reaction was stirred protected from light for 24 hours at 30° C. The reaction was purified by HPLC with a triethylammonium acetate (TEAA) gradient.

Example 8

Preparation of Conjugates of the Invention: Coupling to a Diagnostic Contrast Agent (DTPA)

The performance of contrast agents in MRI imaging methods benefits from the non-covalent binding to serum albumin both in terms of increased blood half-life and shorter relaxation times. The contrast agent DTPA is conjugated to a compound of the invention by the following method to yield a conjugate of the invention.

2-(R)-hydroxymethyl-DTPA-penta-tert-butyl ester is converted to 2-(R)-aminomethyl-DTPA-penta-tert-butyl ester by first converting the hydroxyl-group to an azide by stirring for 12 hours with equimolar amounts of diethyl azodicarboxylate, PPh3 and diphenyl phosphoryl azide in THF followed by reduction to the amino group by stirring for 12 hours with Pd/C/H2 in methanol. For conjugation to 2-(R)-aminomethyl-DTPA-penta-tert-butyl the primary amino group of 428-ϵ-Lys-α-$NH_2$ is converted to a thiol group by reaction with dithioglycolic acid activated by EDC/NHS and subsequent reduction with TCEP. 2-(R)-aminomethyl-DTPA-penta-tert-butyl, N-(c-maleimidobutyryloxy) succinimide ester (GMBS) and the thiol derivative of 428-ϵ-Lys-α-$NH_2$ (ratio 1:2:10) are stirred for 12 h at 30° C. The tert-butyl protecting group of the carboxylic acids is removed with TFA. The resulting 428-ϵ-Lys-α-GMBS-DTPA conjugate can be subsequently loaded with Gd and used for MRI studies.

In one instance, 428-D-Lys-β-Ala-DTPA-Gd was synthesised as follows: Fmoc-β-Ala was conjugated to 428-D-Lys with EDC/NHS and deprotected with 5 M KOH as described above. 19 μmol of 428-D-Lys-β-Ala and 14 μmol of p-SCN-Bn-DTPA (Macrocyclics) were dissolved in 120 μl DMSO.

72 μmol of TEA were added. The reaction was stirred for 24 hours at 30° C. The reaction was purified by HPLC with a 100 mM TEAA gradient. Complex formation between 428-D-Lys-β-Ala-DTPA and Gd3+ was performed by adding 10 μmol of $GdCl_3$ to 1 μmol 428-D-Lys-β-Ala-DTPA and adjusting to pH 10 with NaOH, followed by overnight incubation at 25° C. Removal of excess $Gd^{3+}$ was performed by HPLC on a TEAA gradient. As usual, the end products were characterized by mass spectrometry.

Example 9

Preparation of Conjugates of the Invention: Coupling to an Anti-cancer Drug (Doxorubicin)

Doxorubicin is conjugated to 428-ϵ-Lys-α-$NH_2$ via the primary amino group with succinic acid as bifunctional linker. First, doxorubicin is stirred for 12 h at 30° C. with 100× molar excess of succinic anhydride and subsequently purified by HPLC. Thereby the amino group reacts with the succinic anhydride by formation of an amide bond and liberation of a carboxylic acid. This carboxylic acid is activated by equimolar amounts of EDC/NHS for 4 h at 30° C. prior to addition of 10× excess of 428-ϵ-Lys-α-$NH_2$. Purification is performed by HPLC and characterization by mass spectrometry.

For conjugation via the carbonyl group doxorubicin is stirred for 12 h at 30° C. with molar excess of (6-maleimidocaproyl)hydrazide. The primary amino group of 428-ϵ-Lys-α-$NH_2$ is converted to a thiol by reaction with dithioglycolic acid activated by EDC/NHS and subsequent reduction with TCEP. The doxorubicin-hydrazone-caproyl-maleimide is coupled to the thiol-derivative of 428-ϵ-Lys-α-$NH_2$ by stirring with 10-fold excess of thiol derivative for 12 h at 30° C.

Example 10

Preparation of Conjugates of the Invention: Coupling to a Cancer Drug (Epithilone)

Epothilones are potent drugs in the field of cancer therapy. However, the main limitation in administration of epothilones is their neurotoxcity. Since the binding to serum albumin significantly decreases the ability of the drug to penetrate the blood-brain barrier, conjugation of epothilones to an albumin-binding molecule is a powerful approach to reducing side-effects, allowing higher dosages and thus increasing their therapeutic efficacy.

The conjugation of 428-ϵ-Lys-α-$NH_2$ to epothilones follows a protocol that is equivalent to that described for doxorubicin in Example 9. First 428-ϵ-Lys-α-$NH_2$ is converted to the thiol derivative as described in Example 9 for doxorubicin. The epothilone, (6-maleimidocaproyl)hydrazide and the thiol derivative of 428-ϵ-Lys-α-$NH_2$ are stirred for 12 hours at a molar ratio of 1:2:10. A protection strategy may be adopted in order to prevent side reaction with the epoxide group of the epothilone.

Example 11

Characterisation of Compounds and Conjugates of the Invention by Isothermal Titration Calorimetry (ITC)

In-solution measurements of binding affinities were performed by isothermal titration calorimetry (ITC).

Figure 3:
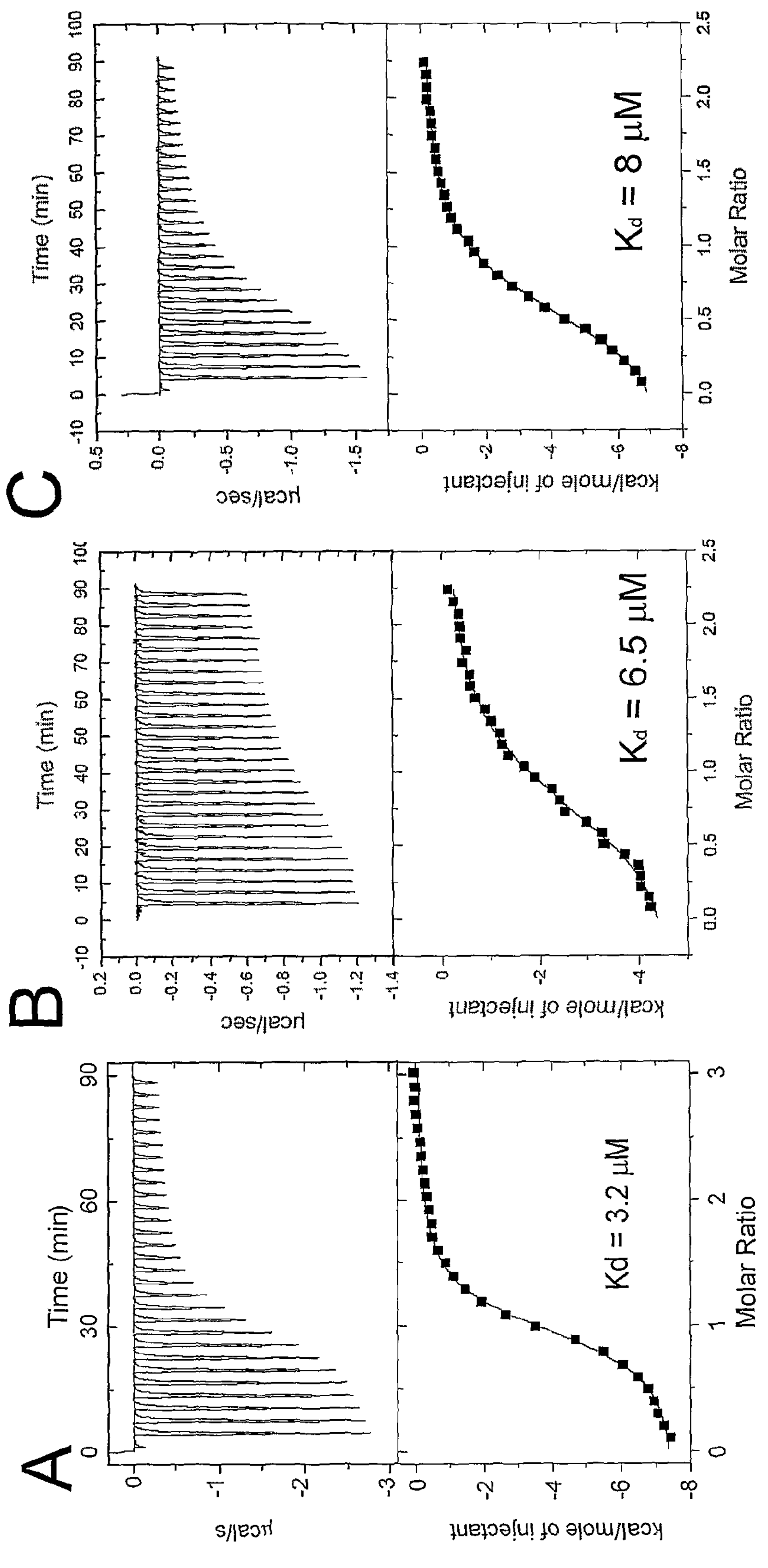
FIG. 3 shows the results of isothermal titration calorimetry (ITC) measurements of 428-ϵ-Lys-α-NHAc (A), 428-ϵ-Lys-α-NH-FITC (B) and 428-aminoheptanoic acid-α-Lys-ϵ-NHAc (C).

The binding experiments by ITC were performed following the procedure of reference 34. 1×2 μl, followed by 29×20 μl, of 428-derivative were injected into 1.8 ml of human serum albumin. All ITC measurements were carried out at concentrations of 50-100 μM protein and 0.5-1 mM conjugate, in PBS, 2% DMSO at 37° C. ITC measurement of the 428-aminoheptanoic acid of Example 1 revealed a dissociation constant of $K_d$=3 μM to two binding sites comparable in affinity. Modification of the primary amino group in 428-aminoheptanoic acid-α-Lys-ϵ-$NH_2$ and 428-ϵ-Lys-α-$NH_2$ with acetic and butanoic acid did not significantly alter the binding affinity towards HSA ($K_d$=3.2 μM for 428-ϵ-Lys-α-NHAc, $K_d$=5.5 μM for 428-ϵ-Lys-α-NHBu, $K_d$=8 μM for 428-aminoheptanoic acid-α-Lys-ϵ-NHAc, $K_d$=8 μM for 428-aminoheptanoic acid-α-Lys-ϵ-NHBu to a single binding site on humans serum albumin) (see FIG. 3). This confirmed the desired characteristics of a universal "chemical handle" that may used to conjugate a wide range of agents to the compounds of the invention. 428-ϵ-Lys-α-NHAc also bound the serum albumin of other species. Murine serum albumin was recognised with similar affinity ($K_d$=3.7 μM and 3.6 μM in two separate measurements) whereas the affinity towards rat serum albumin was 6× lower ($K_d$=28 μM).

Figure 8:
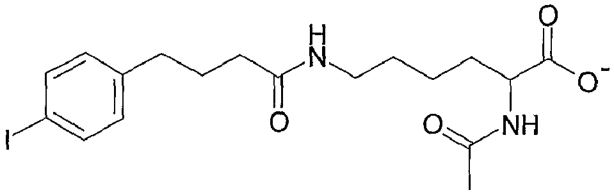
FIG. 8 shows a structure-activity relationship study of albumin binding (ITC)
Figure 8:
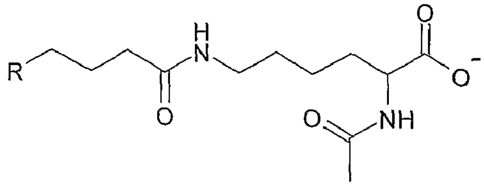
Figure 8:
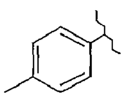
Figure 8:
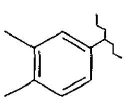
Figure 8:
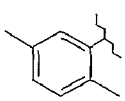
Figure 8:
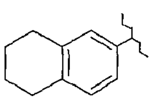
Figure 8:
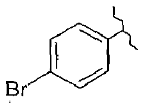
Figure 8:
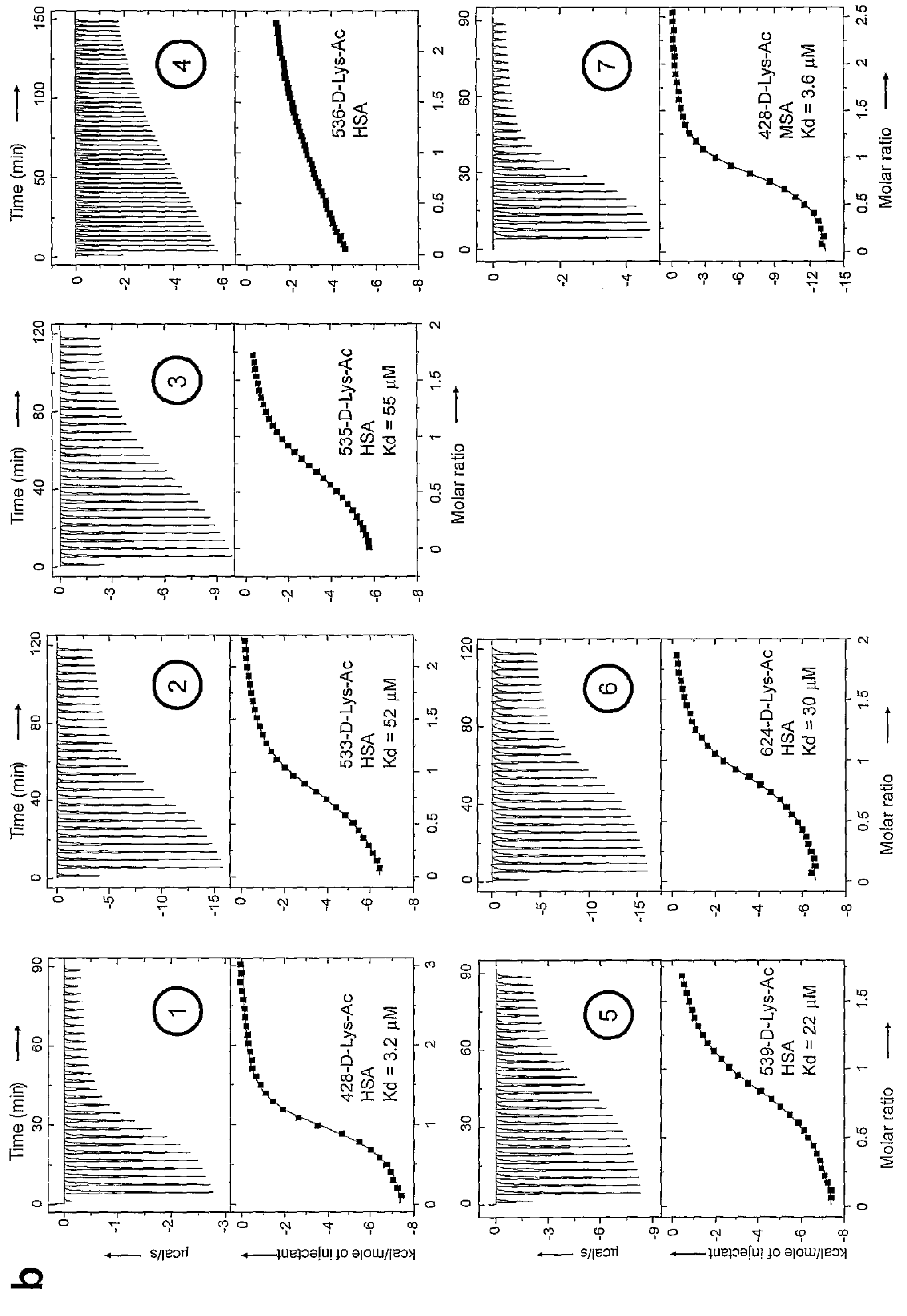

Structure-activity-relationship of albumin binding was further characterised by ITC in a series of measurements shown in FIG. 8 The Figure shows a general structure for the molecules X-D-Lys-Ac measured by ITC (X=533, 535, 536, 539 and 624). The binding of 428-D-Lys-Ac (1) and the other identified binding molecules (wherein 2, 3, 4, 5 and 6 correspond to structures 533, 535, 536, 539 and 624, respectively) to HSA was characterized.

Additionally, FIG. 8 shows a measurement of the affinity of 428-D-Lys to MSA (7), which was comparable to the corresponding measurement with HAS (1).

The other tested binders (X=533, 535, 536, 539 and 624) conjugated to acetylated D-lysine had affinities in the micromolar range. The ranking of their dissociation constants was found to correspond with relative retention in the chromatographic albumin binding assay (see below, Example 17).

Conjugation of the α-amino group of 428-ϵ-Lys-α-$NH_2$ to FITC did not lead to any substantial loss of albumin-binding affinity. After conjugation to FITC the binding affinity to human serum albumin remained similar when determined by ITC ($K_d$=6.5 μM, see FIG. 3).

Figure 9:
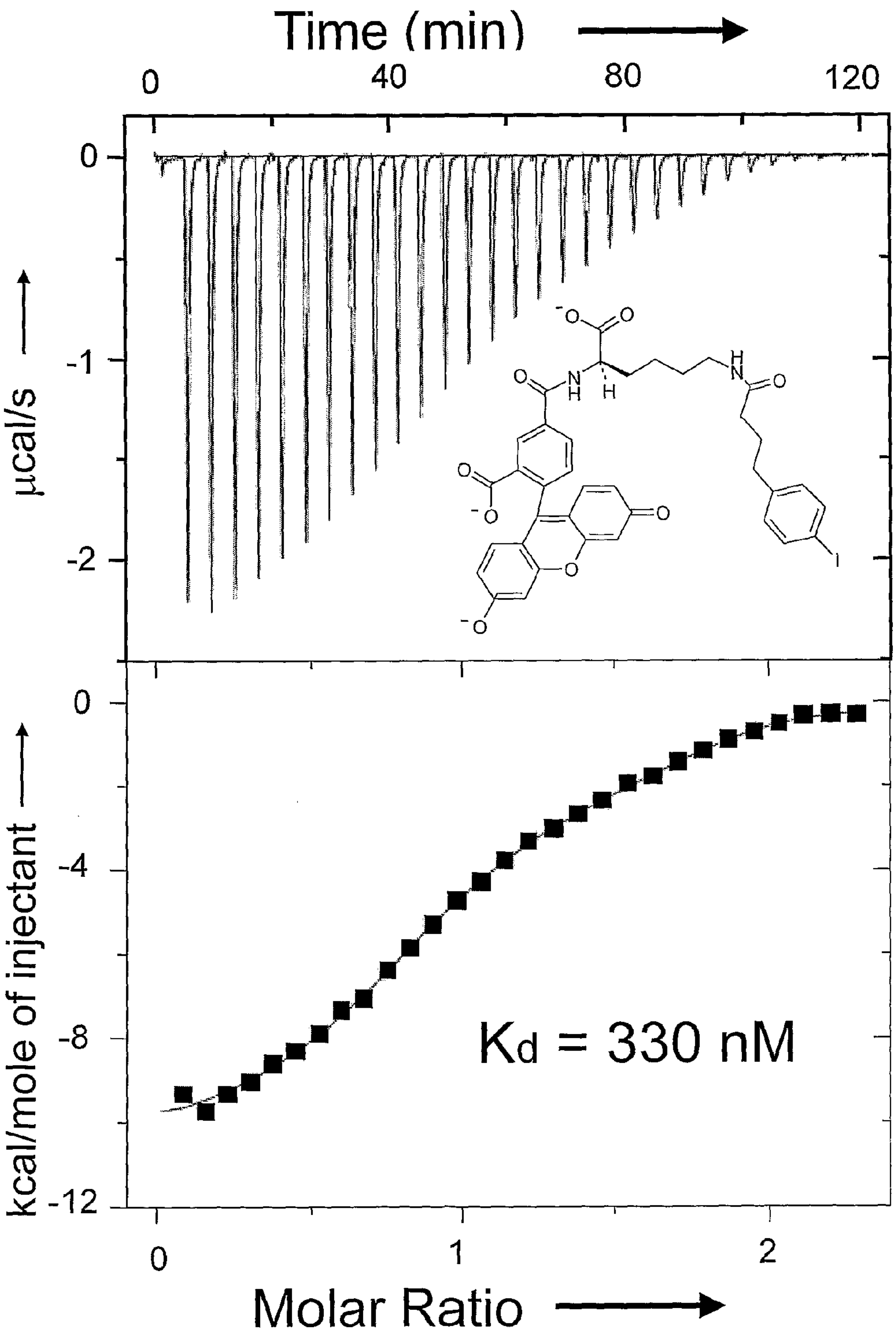
FIG. 9 shows the measurement of the $K_d$ value of a fluorescein amide conjugate according to the invention (428-D-Lys-FAM) by ITC

Moreover, fluorescein and several fluorescein derivatives (428-D-Lys-FAM, 622-D-Lys-FAM, and phenethylamine-FAM) were characterized. The dissociation constant of 428-D-Lys-FAM to HSA measured by ITC at 37° C. was 330 nM (FIG. 9).

Figure 10:
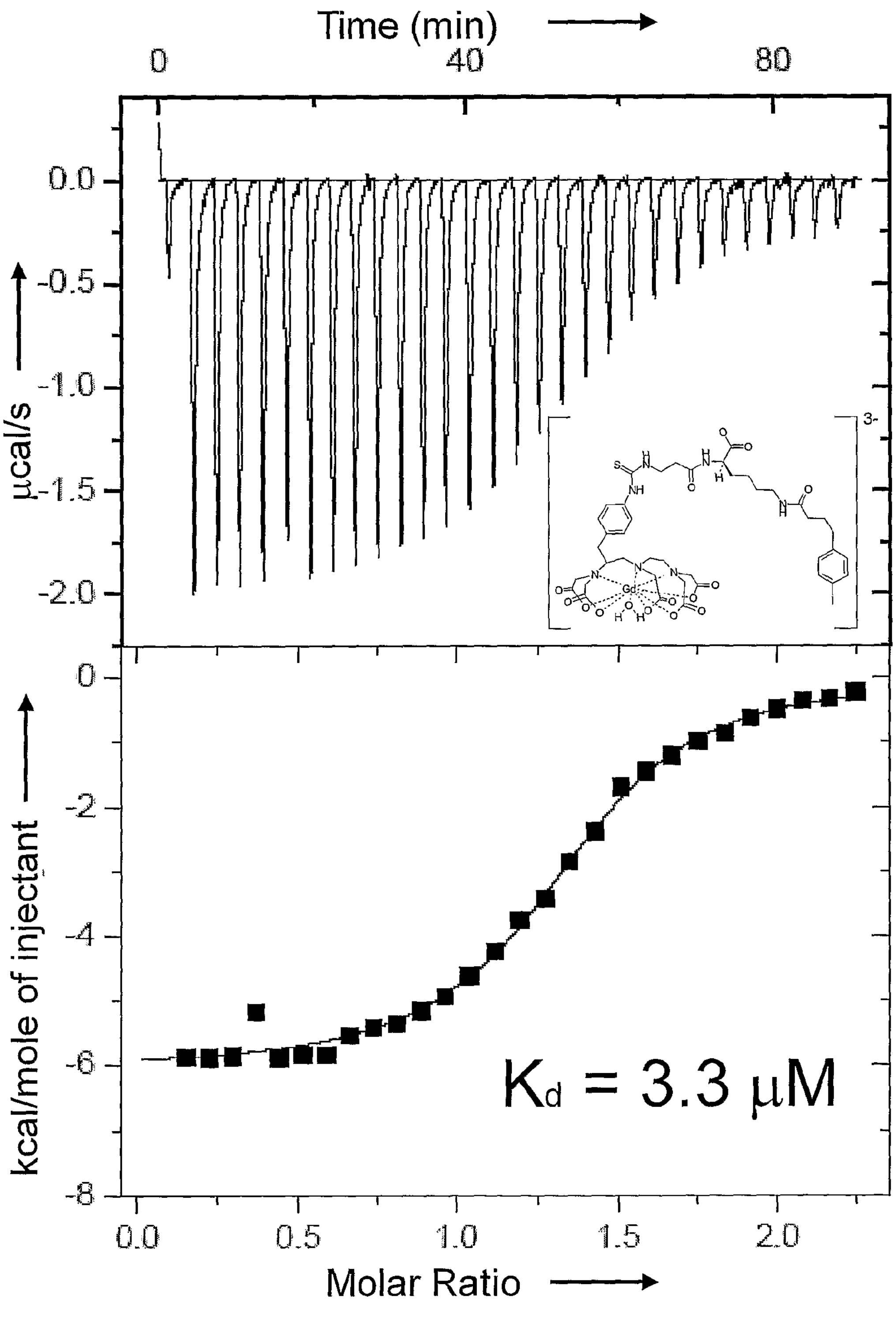
FIG. 10 shows the measurement of the $K_d$ value of a Gd-DTPA-conjugate according to the invention (428-D-Lys-βAla-DTPA-Gd) by ITC

Moreover, the affinity of 428-D-Lys-βAla-DTPA-Gd to HSA was determined by ITC ($K_d$=3.3 μM, FIG. 10). As explained above, DTPA (diethylenetriamine-pentaacetic acid) is a common chelator in nuclear medicine procedures and Gd-DTPA is the most widely used contrast agent in MRI.

Generally, isothermal titration calorimetry measurements were performed using a VP-ITC instrument (Microcal). Fatty acid free HSA (Sigma, A1887) or fatty acid free MSA (A1056) was dissolved in PBS, 2% DMSO and dialyzed against the identical buffer. The concentration of protein for the experiment varied between 30 μM to 1 mM. The experiments were generally performed by titrating serum albumin with the binding molecules. HSA or MSA was titrated with a solution of binding molecule roughly ten fold higher in concentration than the protein solution in PBS, 2% DMSO at 37° C. Typically, titrations were performed until a ratio of 2:1 of ligand to binding sites on protein was reached. Ligands were dissolved in the dialysis buffer. The precise concentration of binding molecule was determined by HPLC/UV. The resulting titration curves were processed and fitted with the Origin 7 software (Microcal) to obtain Kd and ΔH values.

Example 12

Characterisation of Compounds and Conjugates of the Invention by Fluorescence Polarisation 100 nM of 428-D-Lys-FAM, 622-D-Lys-FAM and, for comparison, of fluorescein and of phenethylamine-FAM were incubated with increasing amounts of HSA in PBS for 1 h at 25° C. The fluorescence polarization was determined by excitation at 485 nm and measurement at 535 nm.

Figure 11:
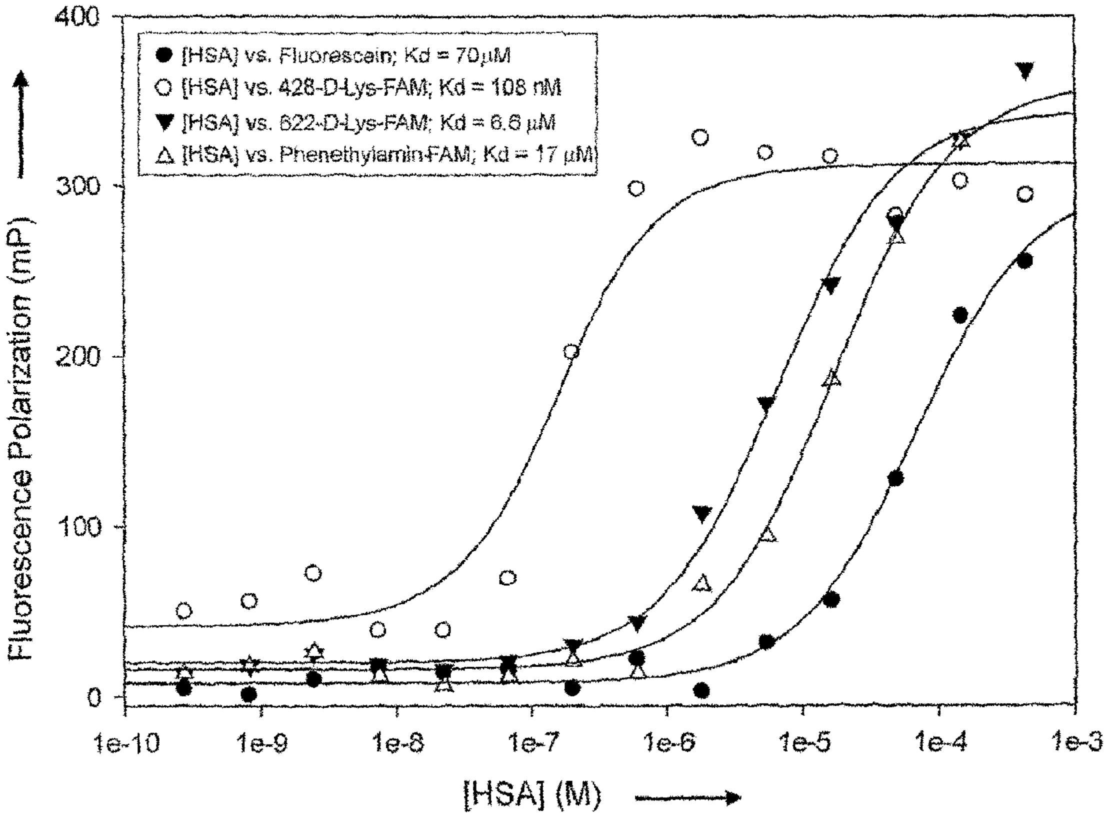
FIG. 11 shows the measurement of $K_d$ values by fluorescence polarisation.

The dissociation constants thus measured were 76 μM for fluorescein, 108 nM for 428-D-Lys-FAM, 6.6 μM for 622-D-Lys-FAM and 17 μM for phenethylamine-FAM (see FIG. 11)

Example 13

Characterisation of Compounds and Conjugates of the Invention by Fluorescence Polarisation in Competition Experiments 500 nM of 428-D-Lys-FAM and HSA were incubated with 1 μM, 10 μM and 100 μM of various HSA-binding competitors in PBS for 1 h at 25° C. Fluorescence polarization was determined by excitation at 485 nm and measurement at 535 nm.

These competition experiments suggest that of 428-D-Lys-FAM binds HSA at site II. FIG. 12 summarises the results obtained by fluorescence polarization of competition for 428-D-Lys-FAM binding. 500 nM of 428-D-Lys-FAM and HSA were incubated with increasing amounts of competitor (left panel). The control values for unbound (no HSA) and bound (no inhibitor) 428-D-Lys-FAM are given (right panel).

Example 14

Figure 4:
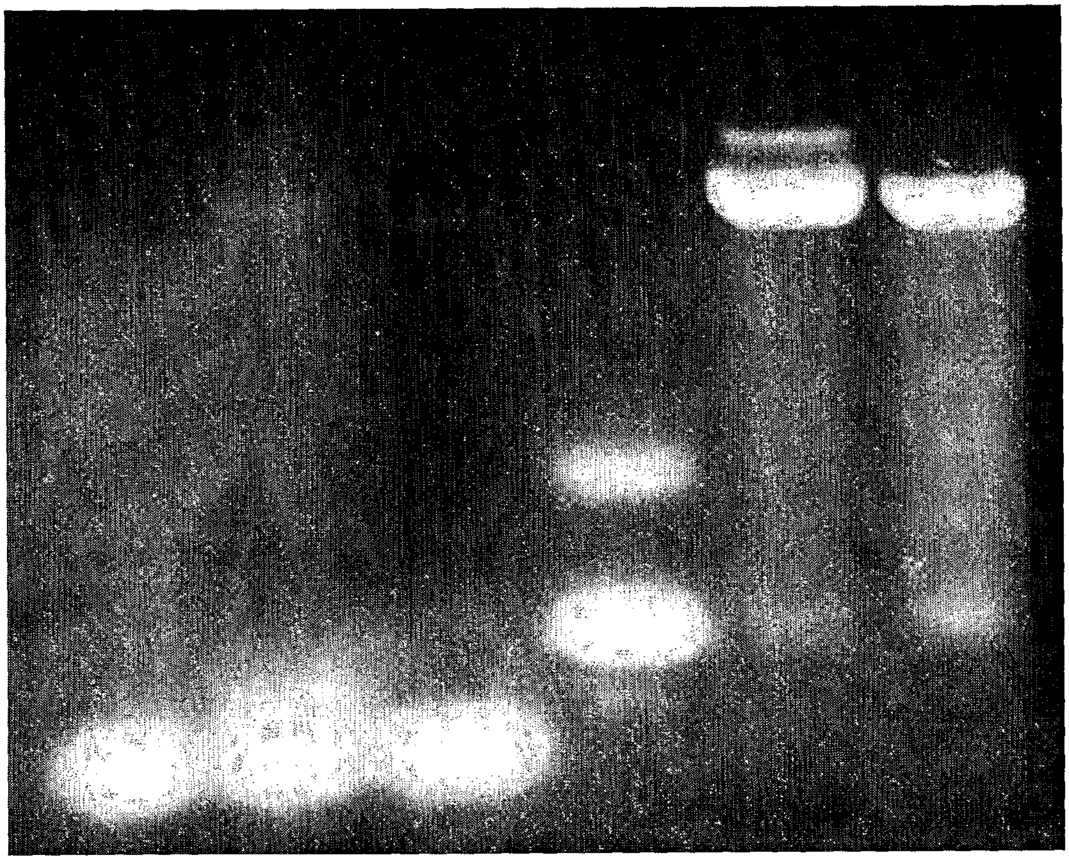
FIG. 4 shows the electromobility shift obtained in the comparison of fluorescein (A) and 428-ϵ-Lys-α-NH-FITC (B), each either alone (–) or preincubated with human serum albumin (HSA) and human serum (Serum).

Characterisation of Compounds and Conjugates of the Invention by a Electro-Mobility Shift Assay An electro-mobility shift assay was carried out following the general protocol of reference 35. 10 μM fluorescein or 10 μM 428-ϵ-Lys-α-NH-FITC were each preincubated in 10 ul, in PBS buffer [36], with either 100 μM human serum albumin or human serum (diluted 1/5). The assay incubation time was 30 min. Polyacrylamide gel electrophoresis [35, 36], was carried out using a 20%-acrylamide gel preparation, TBE (Tris/Borate/EDTA) buffer [36], and a sample loading volume of 10 ul in 5% sucrose. The running conditions were 180 V/40 min. The electro-mobility shift assay demonstrated the binding of 428-ϵ-Lys-α-NH-FITC and its specificity for HSA (FIG. 4).

Figure 13:
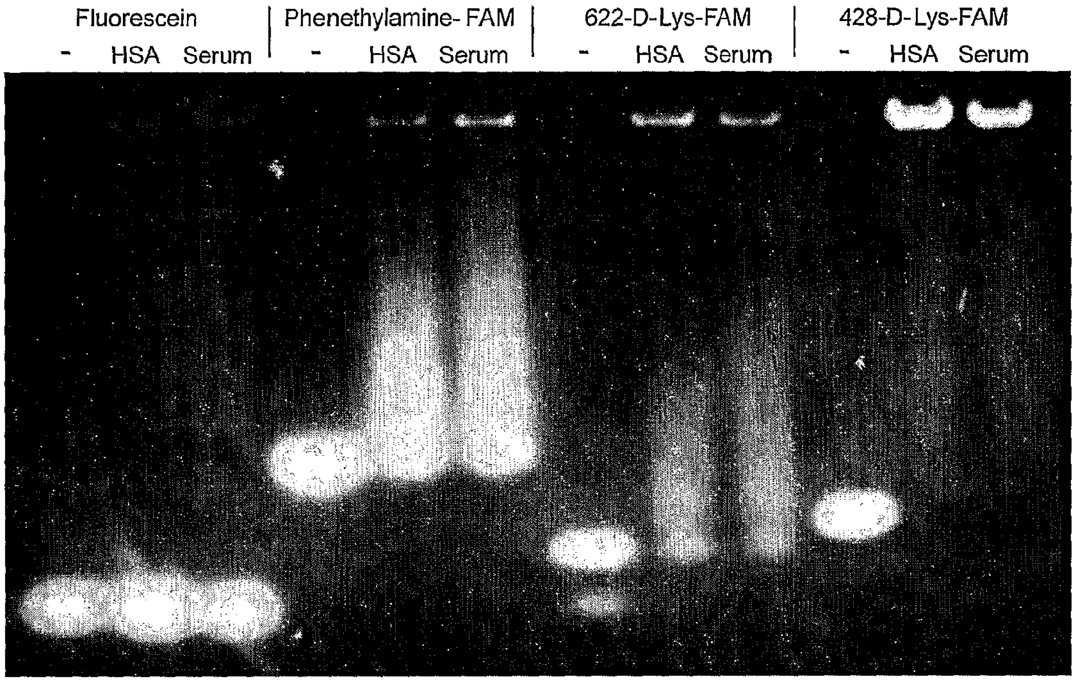
FIG. 13 shows the electromobility shift obtained in the comparison of fluorescein, phenethylamine-FAM, 428-D-Lys-FAM, and 622-D-Lys-FITC, each either alone (–) or preincubated with human serum albumin (HSA) and human serum (Serum)

In a further series of electro-mobility shift experiments (see FIG. 13), fluorescein, phenethylamine-FAM, 428-D-Lys-FAM, and 622-D-Lys-FAM at a concentration of 5 μM were incubated with PBS, HSA (50 μM) and human serum (10× diluted in PBS) in PBS. After one hour the samples were loaded onto a 20% polyacrylamide gel and run for 40 minutes at 180 V in Tris/Borate/EDTA pH 8.2

Example 15

Evaluation of Pharmacokinetic Properties of Conjugates of the Invention

The pharmacokinetic properties of conjugates of the invention are evaluated by injection of both said conjugate and the corresponding unconjugated agent (i.e. the agent that has not been modified by a compound of the invention) into mice and subsequent sampling of the conjugate and agent concentrations. Conjugate and agent concentrations are determined by Liquid Chromatography/Mass Spectrometry/Mass Spectrometry (LC-MS/MS) according to techniques known in the art [37].

Figure 5:
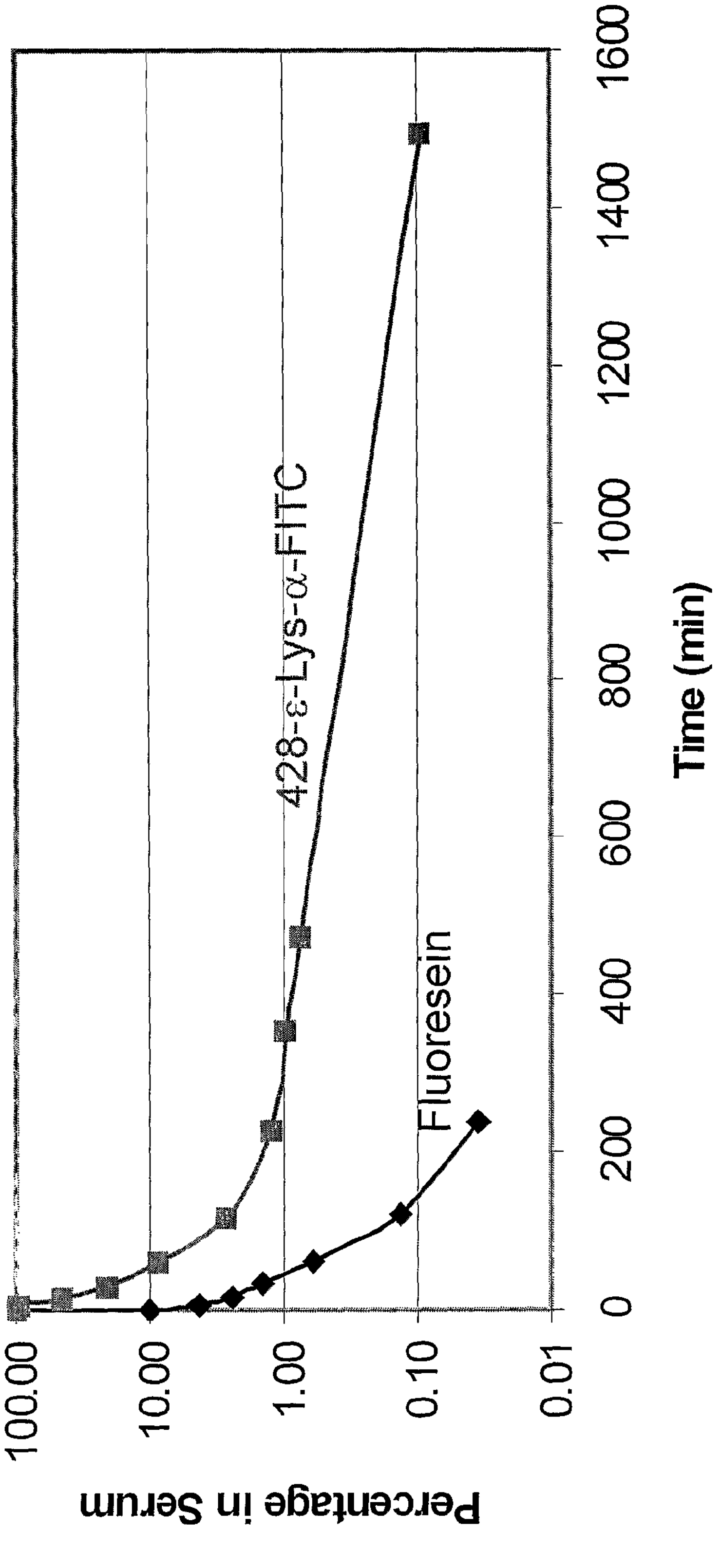
FIG. 5 shows the pharmacokinetic profile of 428-ϵ-Lys-α-NH-FITC vs. fluorescein.

100 μl of a 170 μM solution of fluorescein and of 428-ϵ-Lys-α-NH-FITC were injected into 2 pairs of immunocompetent 129SV mice. The concentration of the individual compounds in the serum of the mice sampled at time-points throughout 24 h was determined by LC/MS/MS showing a significantly different pharmacokinetic profile for the two compounds. While fluorescein was rapidly cleared from the serum ($t_{1/2}$=12.5 min), 428-ϵ-Lys-α-NH-FITC remained in the serum for a significantly longer period of time displaying a biphasic clearance with a $t_{1/2,\alpha}$=22.5 min and $t_{1/2,\beta}$=340 min (FIG. 5).

Figure 14:
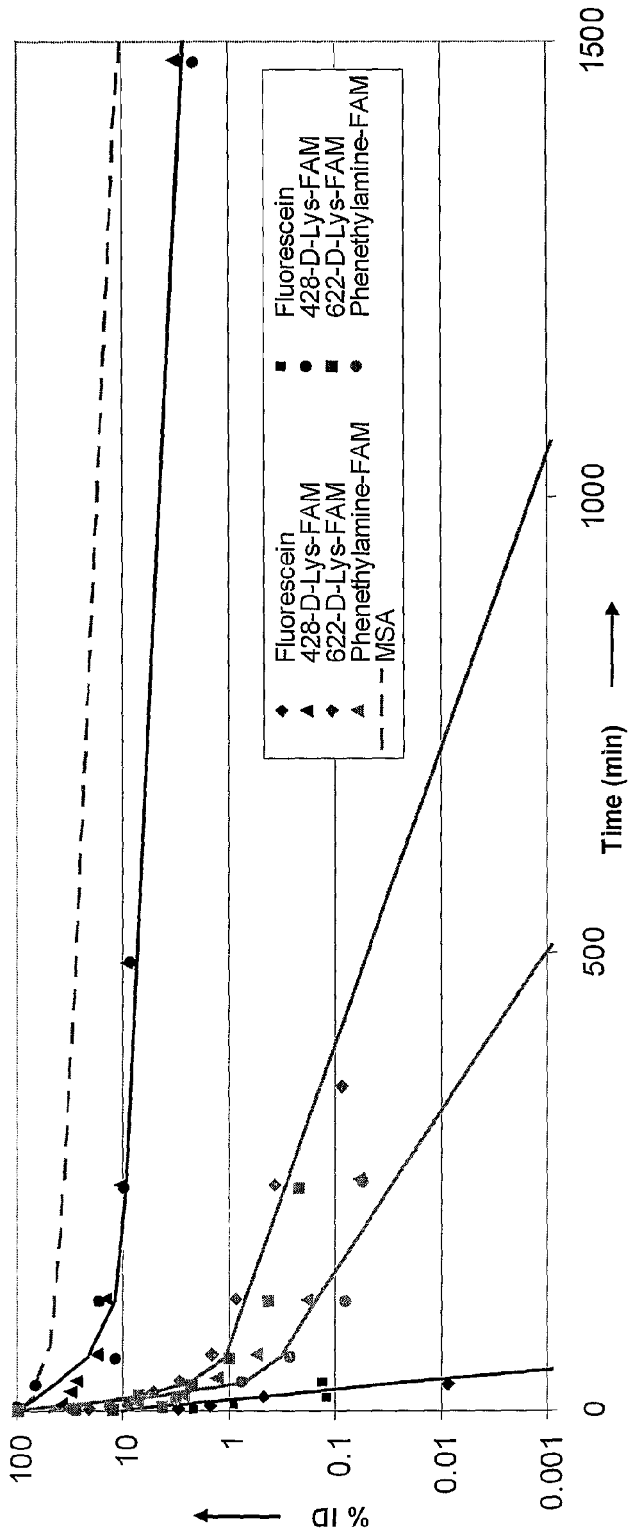
FIG. 14 shows the pharmacokinetic profiles of fluorescein, phenethylamine-FAM, 428-D-Lys-FAM, and 622-D-Lys-FAM in mouse.

In a further in vivo experiment, the pharmacokinetic properties of fluorescein, phenethylamine-FAM, 428-D-Lys-FAM, and 622-D-Lys-FAM were measured and compared. Clearance profiles for the four compounds differed distinctly (FIG. 14). While fluorescein cleared rapidly with a monophasic profile and was no longer detectable 30 minutes after injection, the derivatives displayed a biphasic clearance profile in correlation with their affinities towards HSA (fluorescein: t1/2=4.6 min; 428-D-Lys-FAM: t1/2, α=27 min, α-phase=90%, t1/2, β=495 min; 622-D-Lys-FAM: t1/2, α=5.3 min, α-phase=98%, t1/2, β=100 min; phenethylamine-FAM: t1/2, α=5 min, α-phase=99.5%, t1/2, β=53 min).

Pharmacokinetic analyses were performed under the Project Licenses 198/2005 of the Veterinaramt des Kantons Zürich (issued to Dario Neri). 129SvPas mice were injected into the tail vein with 20 nmol of fluorescein, Phenethylamine-FAM, 428-D-Lys-FAM, or 622-D-Lys-FAM dissolved in 100 μl of 100 mM Tris/HCl, 105 mM NaCl, pH 8.2 (2 mice each). 20-30 μl blood samples were taken from the vena saphena with EDTA coated capillaries (Sarstedt) 1, 5, 15, 30, 60, 120, 240, 360, 480 and 1440 minutes after injection and centrifuged. 5-10 μl of plasma were mixed with 40 μl of 0.1% trifluoroacetic acid and 200 μl of ethanol and incubated on ice for 1 hour. After one hour the samples were centrifuged to remove the precipitated proteins. The supernatant was dried under vacuum and subsequently redissolved in 50 μl of DMSO/H2O. 40 μl were injected into an LC/MS/MS system (Micromass Quattro micro API) and run on a linear gradient from in 0.1% HCOOH from 5% to 95% acetonitrile in ten minutes on a Waters XTerra MS C18 column (3.5 μM, 1×50 mm) while observing the daughter ions with m/z of 287.1 and 202.1 of the parent ion 333.1 for fluorescein, with m/z of 287.3 and 332.3 of the parent ion 480.2 for Phenethylamine-FAM, with m/z of 287.3, 377.2 and 505.2 of the parent ion 777.1 for 428-D-Lys-FAM, and with m/z of 287.3 and 505.4 of the parent ion 651.3 for 622-D-Lys-FAM. Comparing the area under the curve with a previously obtained dilution series of fluorescein and 428-D-Lys-FAM in plasma with identical sample preparation allowed the quantification of the molecules.

Pharmacokinetic profiles were also studied with $^{177}$Lu complexes of DTPA and 428-D-Lys-βAla-DTPA injected i.v. into mice. Similar to the situation encountered with the fluorescein derivatives, DTPA-$^{177}$Lu was cleared rapidly with a monophasic profile and was no longer detectable 60 minutes after injection, while 428-D-Lys-βAla-DTPA-$^{177}$Lu displayed a substantially slower biphasic clearance profile (FIG.

15; 428-DLys-βAla-DTPA-$^{177}$Lu: t1/2, α=22 min, α-phase=90%, t1/2, β=408 min).

Formation of DTPA complexes was performed by incubating 2.25 nmol of DTPA or 428-DLys-DTPA with 70 μCi of $^{177}$Lu (Perkin Elmer) overnight at 25° C. in 250 μl of PBS. Complete complex formation was verified by HPLC using a radioactivity detector (GABI Star, Raytest) with TEAA buffer. 129SvPas mice (2 mice each) were injected with 30 μCi of DTPA-$^{177}$Lu, or 428-D-Lys-β-Ala-DTPA-$^{177}$Lu in 100 μl of PBS into the tail vein. Blood sampling and $^{177}$Lu quantification was performed 1, 5, 15, 30, 60, 120, 240, 480, 1440 min after injection as described above.

To measure the pharmacokinetics of MSA, 75 nmol MSA were labeled with DTPA by reaction with 2.1 μmol p-SCN-Bn-DTPA in PBS for 4 h at 4° C. followed by purification on a PD-10 column (GE Healthcare). 50 nmol MSA-DTPA were labeled with 50 μCi $^{177}$Lu (Perkin Elmer) and purified on a PD-10 column equilibrated in PBS. 3 μC of MSA-DTPA-177Lu were injected into the tail vein of 129SvPas mice (2 mice). Blood sampling was performed 1, 15, 30, 60, 120, 240, 480, 1440 min after injection as described above. The amount of $^{177}$Lu in the injection solution and plasma was quantified by counting on a Packard Cobra γ-counter.

Example 16

Microarray-based Detection of Albumin-binding

The following example provides a microarray-based assay for the detection of whether compounds (e.g. conjugates of therapeutic or diagnostic agents with an albumin-binding domain, or any other molecules) bind albumin. In this assay, which may conveniently be applied to large numbers of compounds in parallel, said compounds are individually and covalently coupled to similar but distinct oligonucleotides that carry an aminohexyl moiety at the 5' extremity [as described in 38]. All these oligonucleotides have an identical sequence at the 5' end, allowing them to be annealed to complementary oligonucleotides, but differ in a portion of 6 bases. This unique, distinct portion acts as a unique “identification code” for each of the organic compounds coupled to a distinct oligonucleotide.

Figure 6:
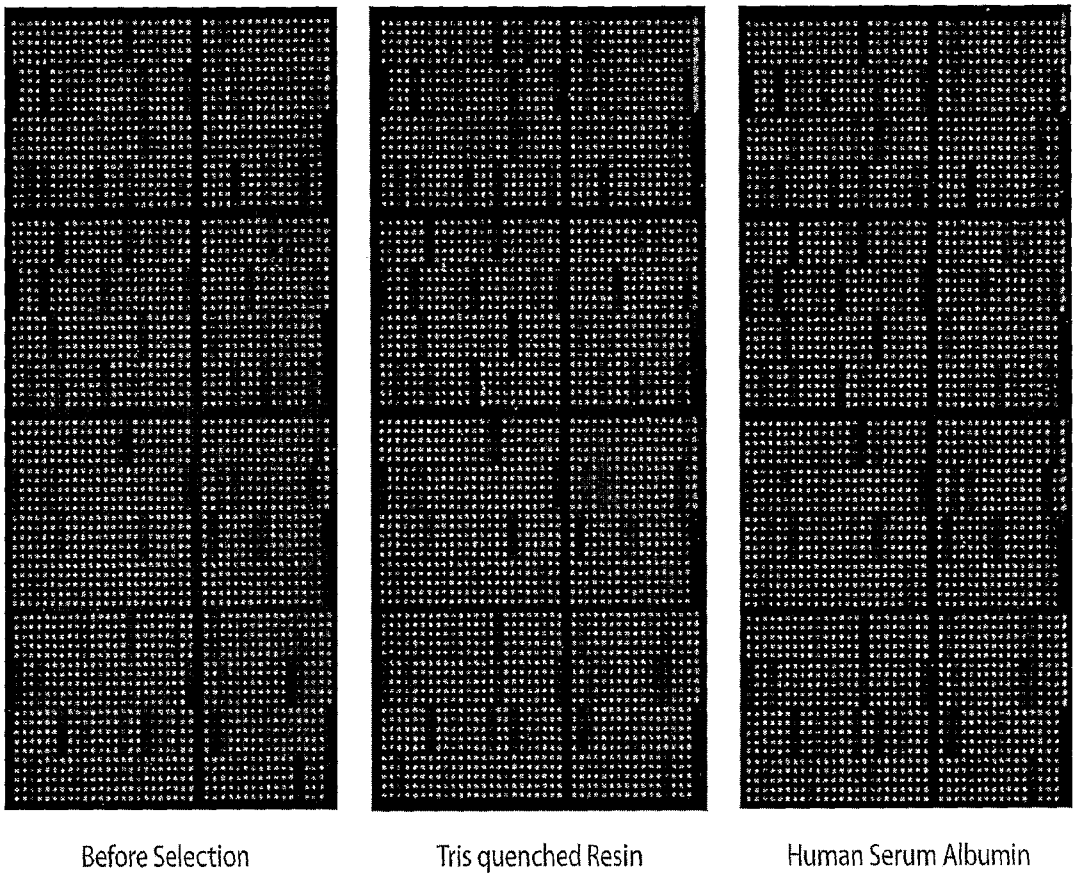
FIG. 6 shows the read-out of a microarray assay for binding to human serum albumin.
Figure 7:
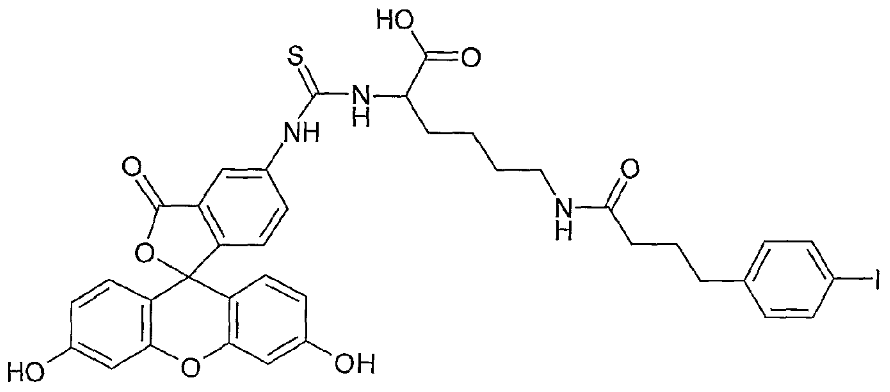
FIG. 7 panels A, B, C show the structures of 428-Lys-FITC, 428-Lys-FAM, and 428-Lys-β-Ala-DTPA-Gd, examples of conjugates of the invention, respectively.
Figure 7:
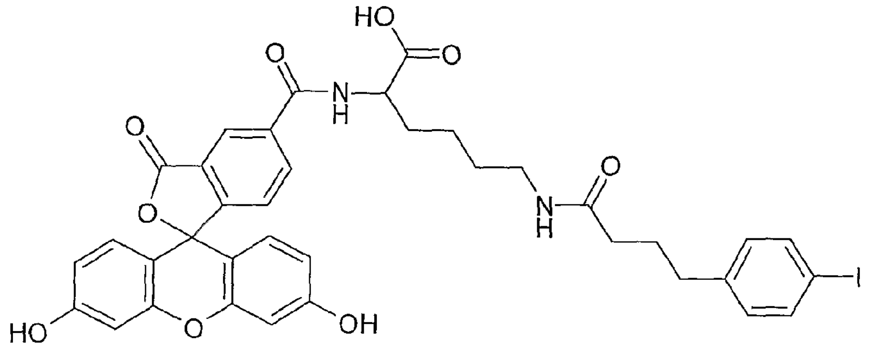
Figure 7:
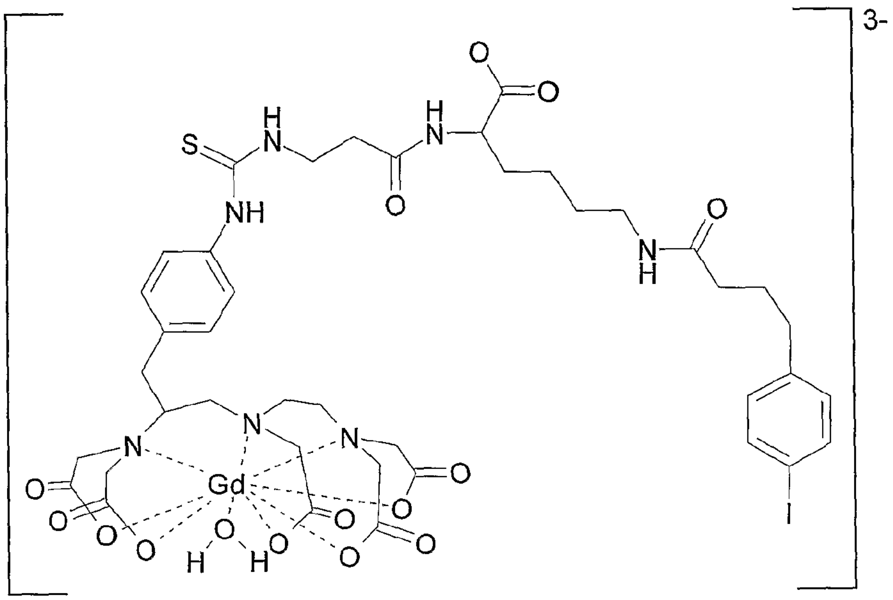

A mixture of the oligonucleotide-compound conjugates to be tested for albumin binding (hereinafter, a “library”) are hybridized to an unmodified 24mer oligonucleotide complementary to the constant region at the 5' end of the oligonucleotides. The dimerisation of the oligonucleotides is achieved by denaturing the oligonucleotides for 3' at 94° C., followed by heteroduplex formation for 10' at 50° C. in 10 mM Tris/Cl, 1 mM $MgCl_2$, pH 8 at final concentrations of 87 nM of library and 120 nM of unmodified pairing oligonucleotides. 10 μl of this assembled library are incubated with 50 μl CNBr-Sepharose modified either with human serum albumin or Tris as a negative control preincubated with 100 μg/ml hering sperm DNA in a total volume of 100 μl for 1 h. After three washing steps with 400 ml of 100 mM $NaH_2PO_4$, 1 mM $MgCl_2$, 0.1% Tween 20, pH 8.5 in SpinX columns the resin is resuspended in 100 μl $H_2O$. The codes of the retained oligonucleotide-compound conjugates are amplified by an exponential PCR of 25 cycles with 5 μl of the resuspended resin. After removal of the unlabeled primers by a PCR Purification Kit (Qiagen) the codes are linearly amplified 25× with a Cy3-labeled primer. The product is precipitated in ethanol and re-dissolved in 120 μL of hybridization buffer (4×SSC, 50 mM HEPES, 0.2% SDS, pH 7) and incubated with microarray glass slides (displaying 19mers with the specific complementary sequences to the 6 base codes of the individual library oligonucleotides in quintuplet) in a Tecan HS 400 hybridization instrument for 4 h at 44° C. followed by successive washing steps with 2×SSC/0.2% (w/v) SDS, 0.2×SSC/0.2% (w/v) SDS, and 0.2×SSC. After hybridization, microarrays are analyzed by using a Genepix professional 4200A scanner (λex 532 nm, 100% laser power, photomultiplier 300). Spot intensities are quantified and evaluated using Genespotter (v2.4.3). After background subtraction, the mean value is used as spot signal intensity (average of five spots). Comparison of the signal intensities after incubation with human serum albumin with intensities after incubation with Tris quenched resin, and with the library before incubation reveals albumin-binding properties of the compounds to be tested (FIG. 6).

Example 17

Characterisation of Albumin Binding Properties by a Quantitative Selection Assay (Chromatographic Albumin Binding Assay)

The binding properties, in particular the albumin-binding selectivity, of compounds and conjugates of the invention may also be analysed by the following quantitative selection assay. A 24mer oligonucleotide complementary to the constant (“identical”) sequence of oligonucleotides such as those of the library of Example 16 is radioactively labelled at the 5' terminus using γ$^{33}$P-ATP and T4 polynucleotide kinase. In separate tubes the radiolabeled oligonucleotide is hybridized either to one of the oligonucleotide-compound conjugates or an unconjugated oligonucleotide as a negative control. The experiments are performed at a duplex concentration of 100 nM. Aliquots of these oligonucleotide duplex pairs are incubated with human serum albumin conjugated to CNBr-sepharose slurry for 1 h and washed as described in the selection procedure. The flow-through of the incubation and the washing steps and the resin are subjected to $^{33}$P radioactivity counting with a Beckman LS 6500 scintillation counter. The count of the radioactivity indicates the relative degree, if any, of retention (i.e., binding) of the oligonucleotide-compound conjugates on the resin.

In one series of experiments, a 24mer oligonucleotide was labeled as described above, using γ$^{33}$P-ATP (GE Healthcare) and T4 polynucleotide kinase (USB). In separate tubes the radiolabeled oligonucleotide was hybridized to one of the selected oligonucleotide-compound conjugates or an unconjugated oligonucleotide as negative control at an oligonucleotide concentration of 100 nM each. Aliquots of these oligonucleotide duplex pairs were incubated with HSA resin in 100 μl of PBS. After 1 h of incubation, three rounds of washing were performed with 400 μl of PBS, and the remaining beads as well as aliquots of the input, flow-through, and all washing fractions were subjected to $^{33}$P radioactivity counting with a Beckman LS 6500 scintillation counter.

Figure 16:
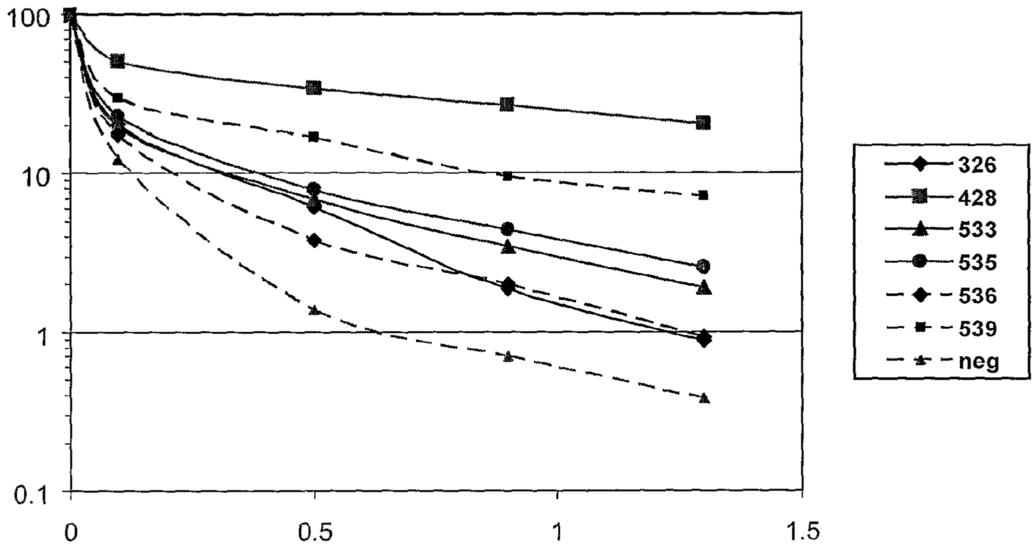
FIG. 16 shows the characterisation of albumin binding properties by a quantitative selection assay (chromatographic albumin binding assay)
Figure 16:
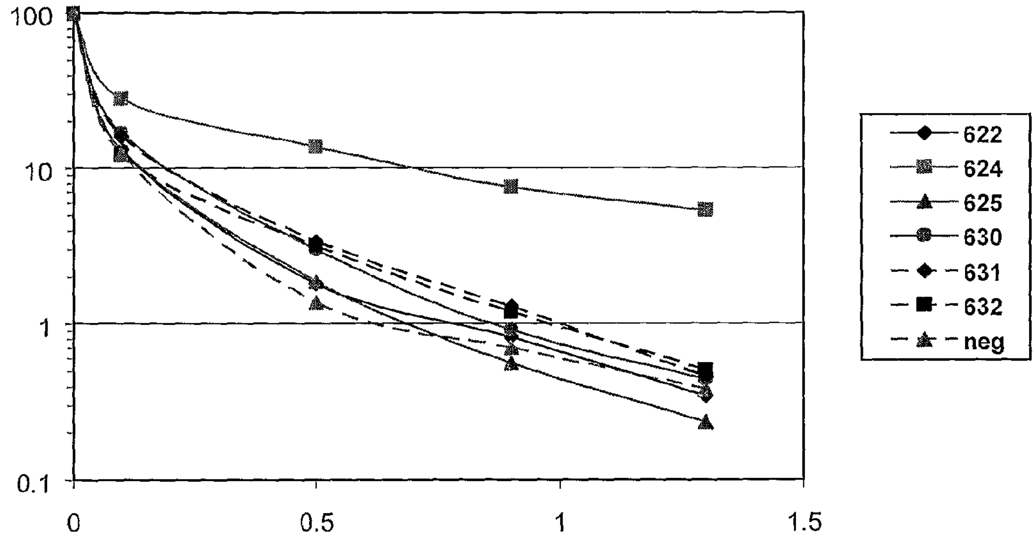

FIG. 16 shows the amount of radioactivity quantified for a selection of albumin-binding moieties throughout several washing steps.

This method is useful for a first classification of binders. Of the binders tested in FIG. 16, it was found that the strongest binders, and their relative strength of binding (ranking) can be described as 428>539>624>535>533>536>326> other binding molecules.

Example 18

Assay of Albumin Removal from Serum

The binding of compounds of interest to albumin and the specificity of said binding for albumin over other proteins in serum may be assessed by coupling compounds of interest as well as bilirubin (a natural HSA ligand with nanomolar affinity), to amino-tagged sepharose.

Human serum albumin and human serum samples (or corresponding animal albumin and serum samples, e.g., mouse, rat, etc.) are incubated with the compound-resin conjugates, or passed over chromatography columns filled with said resin. 1 ml of resin (modified with 100-100× fold molar excess binding molecule over NH2-groups on resin) is incubated with 1 ml HSA (2 mg/ml) in PBS for 30 min. The resin is loaded onto a column and is washed with 3 ml PBS. Elution is performed with 1 ml 8M urea or 100 mM triethylamine.

The results are visualised on protein gels, i.e., serum input, the flow-through or wash from the resin and the elution from the resin are applied to the lanes of a polyacrylamide gel which is subjected to electrophoresis using methods that are known in the art [36]. Evaluation and comparison of said lanes on the resulting after visualisation (e.g., staining and development) of protein bands on the gel [36] reveals the extent of serum albumin removal from serum samples by the various compound-resin conjugates, compared to the bilirubin positive control. In particular the extent to which said compound-resin conjugates remove (and thus bind to) albumin selectively over other proteins contained within serum is revealed.

Example 19

Improved Imaging Performance of Compounds According to the Invention (Angiographic Analysis)

Figure 17:
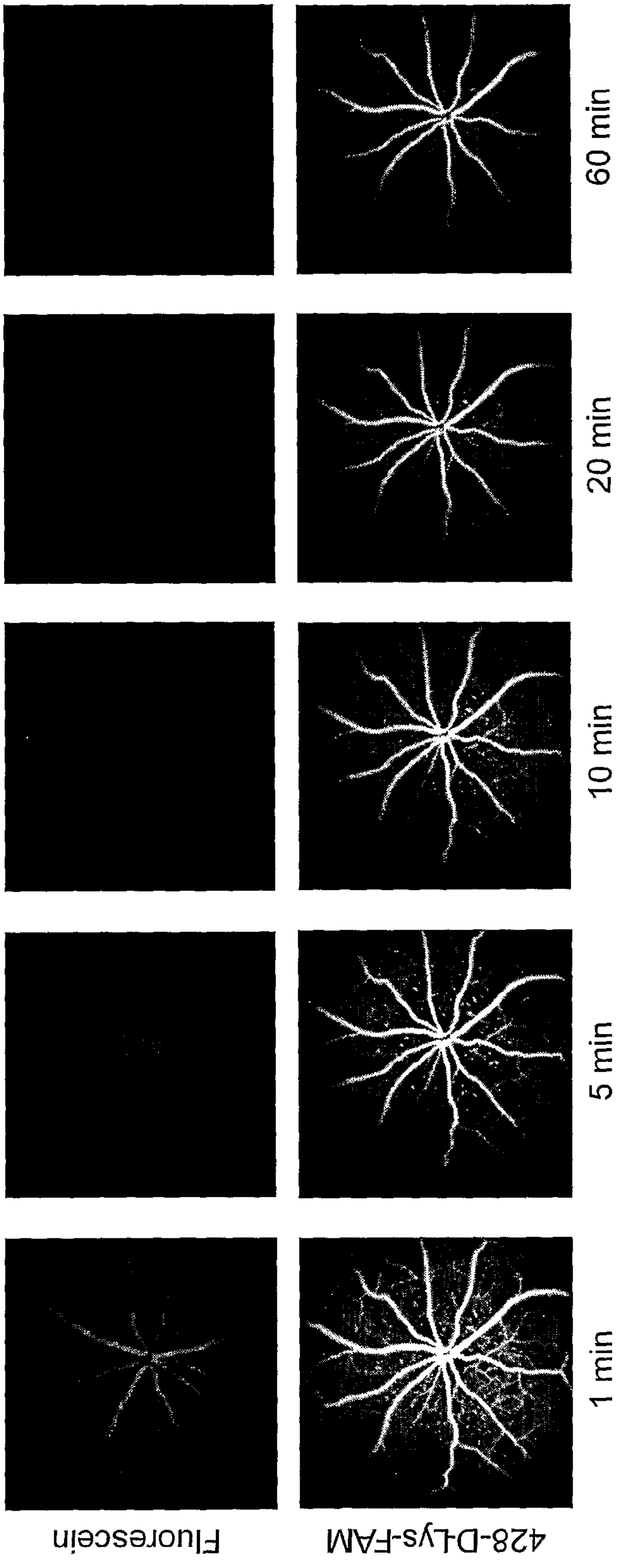
FIG. 17 shows the improved imaging performance of a compound according to the invention (428-D-Lys-FAM) in an angiographic analysis

To obtain functional information on the imaging properties of 428-D-Lys-FAM, a fluorescein angiographic analysis of the retina was performed. Fluorescein and 428-D-Lys-FAM were injected i.v. into mice and pictures of the eye fundus taken at different time-points. The fluorescein angiographic pictures confirmed the results of the pharmacokinetic studies. For fluorescein, the staining of the blood vessels was weak even at early time points and not detectable after 20 minutes. By contrast, the staining of the blood vessels with 428-D-Lys-FAM was longer lasting and allowed the visualization of smaller blood vessels (FIG. 17)

Scanning-laser opthalmoscopy imaging was performed with a Heidelberg Retina Angiograph (HRA I, Heidelberg Engineering, Germany), a confocal scanning-laser opthalmoscope, according to previously described procedures [see reference 39]. Briefly, wild-type C57BL/6 mice were anaesthetized with ketamine (66.7 mg/kg) and xylazine (11.7 mg./kg), and their pupils were dilated with tropicamide eye drops (Mydriaticum Stulln, Pharma Stulln, Germany). The HRA features two argon wavelengths (488 nm and 514 nm) in the short wavelength range and two infrared diode lasers (795 nm and 830 nm) in the long wavelength range. The laser wavelength of 488 nm was used for fluorescein angiography, with a barrier filter at 500 nm. Four mice each received either 50 nmol of fluorescein or 428-D-Lys-FAM dissolved in 100 μl of 100 mM Tris/HCl, 105 mM NaCl, pH 8.2 injected i.v. into the tail. Images were obtained at time-points 1, 5, 20 and 60 minutes after injection applying the same settings of the equipment. In particular, the brightness value in this study was fixed so that the brightest image (428-D-Lys-FAM at 1 minute following injection) could be recorded without overexposure. All examinations were approved by the local authorities (Anzeige v. 13.12.2006, RP Tuebingen) and were performed in accordance with the ARVO Statement for the Use of Animals in Ophthalmic and Vision Research.

Example 20

Improved Imaging Performance of Compounds According to the Invention (MRI Analysis)

To verify the portability of 428-D-Lys as albumin binding moiety a second contrast agent, diethylenetriamine-pentaacetic acid (DTPA), was conjugated to 428-D-Lys (428-D-Lys-βAla-DTPA-Gd) and evaluated. DTPA is a common chelator in nuclear medicine procedures and Gd-DTPA is the most widely used contrast agent in MRI.

Figure 15:
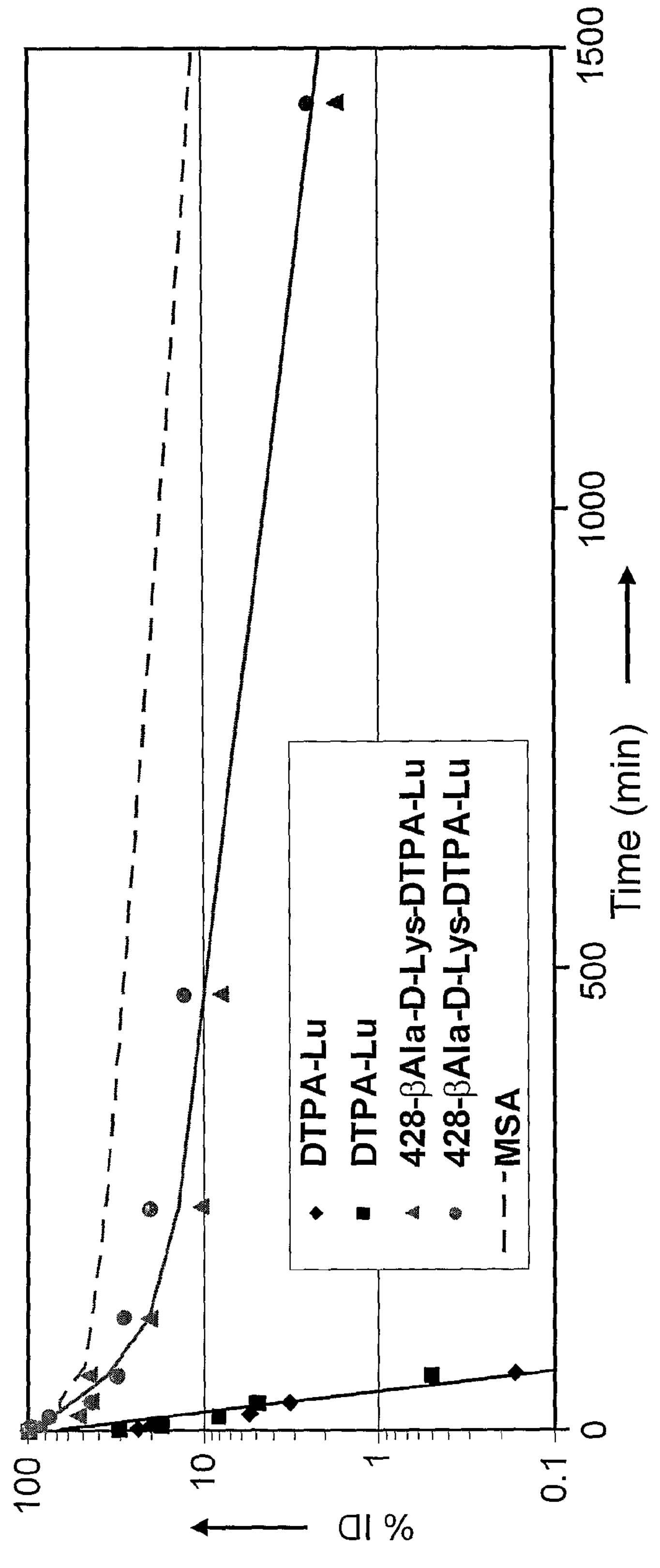
FIG. 15 shows the pharmacokinetic profiles of DTPA-$^{177}$Lu and 428-D-Lys-βAla-DTPA-$^{177}$Lu in mouse
Figure 18:
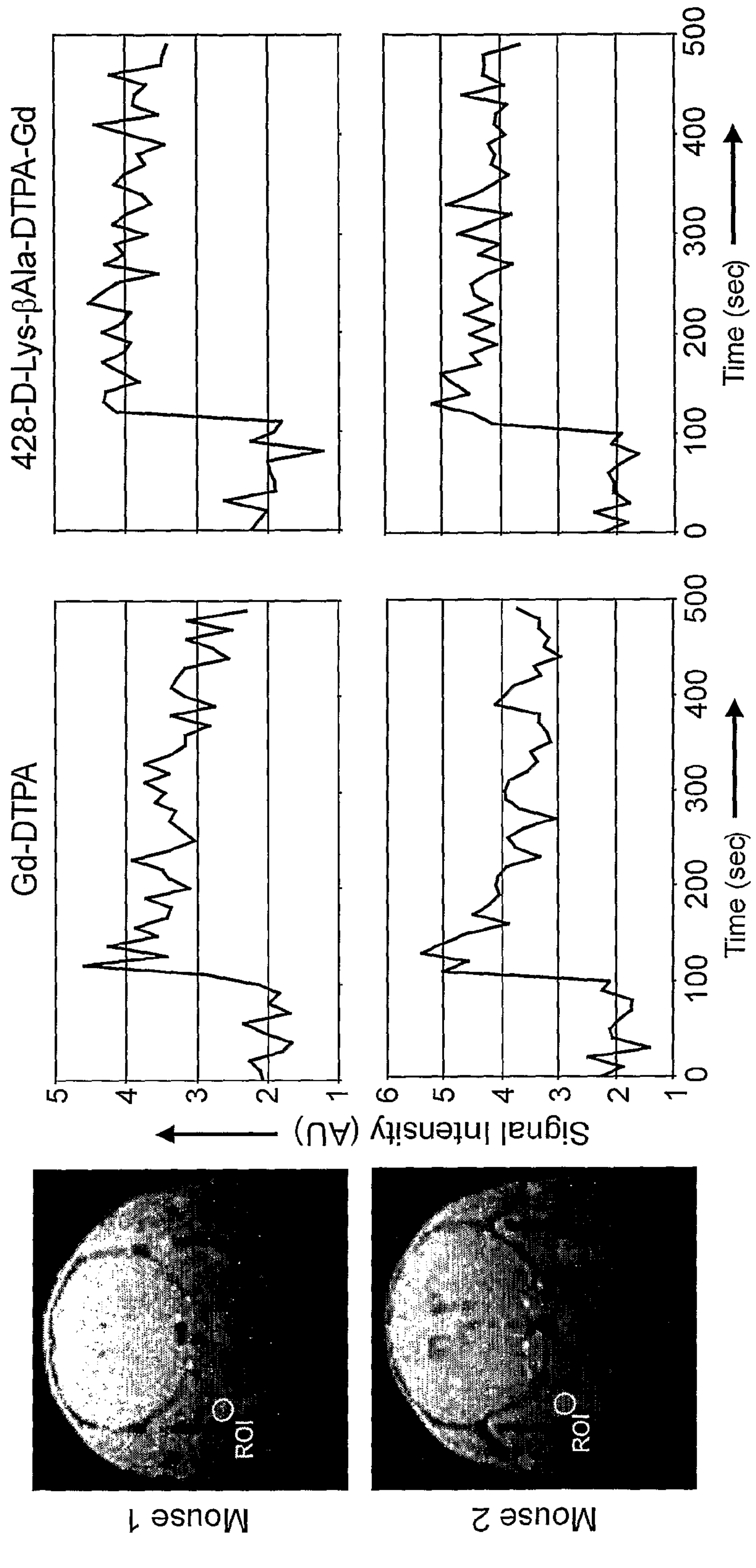
FIG. 18 shows the improved imaging performance of a compound according to the invention (428-D-Lys-βAla-DTPA-$^{177}$Lu) in an MRI analysis.

Rapid extravasation of DTPA-Gd in comparison to slower extravasation of 428-D-Lys-βAla-DTPA-Gd was observed by MRI imaging procedures, following i.v. injection of the contrast agents. MRI analysis of major blood vessels of the brain (FIG. 18) revealed a slower decrease of signal intensities in mice injected with 428-D-Lys-βAla-DTPAGd, consistent with its slower clearance profile (cf. FIG. 15).

All animal experiments were carried out in strict adherence to the Swiss law for animal protection. MR measurements were performed on a Bruker PharmaScan 47/16 MR system (Bruker BioSpin GmbH) operating at 200 MHz using a circular cryogenic surface coil for signal transmission and reception. Mice were anesthetized with 1.4-1.5% isoflurane in air:O2 (4:1). Scout scans were performed to asses the anatomy of the animal. The shortening effect of both contrast agents DTPA-Gd and 428-D-Lys-β-Ala-DTPA-Gd on the longitudinal blood relaxation time (T1) was investigated in two C57/B16 mice. For this purpose, transverse cine 2D images were acquired using the following sequence parameters: field of view (FOV): 19×19×0.5 mm3, matrix size: 128×128, flip angle: 15°, TE/TR: 3.0/14 ms, averages: 6, repetitions: 50, temporal resolution: 10.75 s, total scan time: 8 min 57 s. The inflowing blood was saturated by exciting a 4 mm thick slice (flip angle15°) cranial to the imaging plane. Contrast agents were injected into the tail vein after a baseline of twenty repetitions. Firstly, a dose of 1.2 μmol of DTPA-Gd and secondly, after a wait time of 30 min, a dose of 1.2 μmol of 428-D-Lys-β-Ala-DTPA-Gd was administered. The time course of the MR signal was analyzed in a large vessel and normalized to the baseline value for comparison.

Example 21

HPLC Purification Method

HPLC Purification

All reaction products were purified by HPLC on a Waters XTerra Prep RP 18 column (5 μM, 10×150 mm) using a linear gradient from 0.1% trifluoroacetic acid to acetonitrile or from 100 mM TEAA pH 7 to 100 mM TEAA in 80% acetonitrile, pH 7 in 15 minutes. Unless one gradient is specifically indicated both could be used for purification. After collection of the desired fractions, solvents and buffer were removed under vacuum.

The following references are each incorporated by reference herein in its entirety.

References 1. http://biopharmaceuticals.novozymes.com/files/documents/pres_ds_albfus_2005 nov.pdf
2. Haag et al, Angew Chem Int Ed Engl., 2006, 45, 1198-215.
3. Kratz et al., J Drug Target 2000, 8(5), 305-18.
4. Drevs et al., JCO, 2004, 22, 2125.

5. Janeway C A et al. Immunobiology, 6th edition 2004, Garland, N.Y., ISBN: 0815341016, Chapters 13-21.
6. Dennis et al., J Biol. Chem., 2002, 277, 35035-43
7. WO2005118642
8. WO2006051288
9. EP1517921B
10. Nielson et al., Cancer Res., 2001, 61, 711-6.
11. McLauchlan R, Waterman H, Waterman C, Hillier V, Dodd C. Ethnic variation in fluorescein angiography induced nausea and vomiting. Eye. 2001 Apr.; 15(Pt 2):159-62.
12. PDR for Opthalmology. Montvale, Medical Economy Company, (200) 2 5-2 6
13. McMurry et al. (2002) J. Med. Chem., 45: 3465-3474
14. Parac-Vogt et al. (2005) Chem. Eur. J., 11: 3077-3086
15. Koehler et al, Bioorg Med Chem. Lett., 2002, 12, 2883-6.
16. Lipinski et al., Adv. Drug Del. Rev., 1997, 23, 3-25.
17. Nomenclature of Organic Chemistry, Sections A, B, C, D, E, F, and H, Pergamon Press, Oxford, 1979. Copyright 1979 IUPAC.
18. Borsi et al, 2002 Nov. 1; 102(1):75-85
19. A Guide to IUPAC Nomenclature of Organic Compounds (Recommendations 1993), 1993, Blackwell Scientific publications, Copyright 1993 IUPAC.
20. P. Alessi. "L19 antibody conjugates in cancer and disease"; PhD thesis, ETH Zürich; Nr. 15764.
21. Barrett A J, Rawlings N D, Woessner J F (eds.). Handbook of proteolytic enzymes. 2nd edition 2004, Elsevier Academic Press, Amsterdam; Boston, Mass.
22. The Anticancer Drugs, Oxford University Press, 2nd Edition, Chapter 3, ISBN 0-19-506739-8
23. Ozono S et al. Tumor doubling time of renal cell carcinoma measured by CT. Jpn J Clin Oncol. 2004 February; 34(2):82-5.
24. March's Advanced Organic Chemistry: Reactions, Mechanisms, and Structure. Wiley-Interscience; 5th edition (Jan. 15, 2001) ISBN: 0471585890 and references therein.
25. Bioconjugate Techniques, Academic Press, ISBN: 0-12-342336-8.
26. Lloyd-Williams P, Albericio F, Giralt E. Chemical Approaches to the Synthesis of Peptides and Proteins. CRC Press. 1997. ISBN 0849391423.
27. Benoiton N L. Chemistry of Peptide Synthesis. CRC Press. 2005. ISBN 1574444549.
28. Chan W, White P. Fmoc Solid Phase Peptide Synthesis. Oxford University Press. 2000. ISBN: 0199637245.
29. Kullmann W. Enzymatic Peptide Synthesis. CRC Press. 1987. ISBN 0849368413.
30. FDA (US Food and Drug Administration) web page. Inactive Ingredient Guide.
1996. http://www.fda.gov/cder/drug/iig/default.htm
31. Ash M and Ash I. Handbook of Pharmaceutical Additives. Synapse Information
Resources. 2nd Edition. 2002. ISBN 1890595349
32. Gennaro A R (ed.). Remington: The Science and Practice of Pharmacy. Lippincott Williams & Wilkins. 21st edition. Jul. 3, 2005. ISBN 0781763789.
33. Hardman J G, Limbird L E, Alfred G. Gilman A G. Goodman & Gilman's The Pharmacological Basis of Therapeutics. McGraw-Hill; 10th edition. Aug. 13, 2001. ISBN 0071354697.
34. Pierce et al, Methods. 1999 Oct.; 19(2):213-21
35. Fried et al 1981. Nucl. Acids Res. 9:6505-6525
36. Current Protocols in Molecular Biology ed.: Frederick M. Ausubel et al. New York, John Wiley & Sons Inc (3 Feb. 2004). ISBN: 047150338X
37. Mano et al, Anal Biochem. 1997 Jan. 15; 244(2):291-300
38. Dumelin C E et al., Bioconjugate Chem., 2006, 17, 366-370.
39. Seeliger M W, Beck S C, Pereyra-Munoz N, Dangel S, Tsai J Y, Luhmann U F, van de Pavert S A, Wijnholds J, Samardzija M, Wenzel A, Zrenner E, Narfstrom K, Fahl E, Tanimoto N, Acar N, Tonagel F. In vivo confocal imaging of the retina in animal models using scanning laser opthalmoscopy. Vision Res. 2005 December; 45(28):3512-9.

The invention claimed is:

1. A compound represented by the following formula:

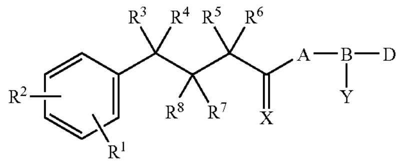

wherein X is O or S;

A is NH, O, S or $CR^9R^{10}$;

D is selected from the group consisting of $OPO_3H_2$, $PO_3H_2$, $OSO_3H$, $SO_3H$, COOH and the conjugate bases thereof;

$R^1$ and $R^2$ are independently selected from the group consisting of H, F, Cl, Br, I, branched, unbranched or cyclic $C_1$-$C_{10}$ hydrocarbyl groups, $OR^9$, $OCOR^9$, $COOR^9$, $CH_2OR^9$, CHO, $COR^9$, $NR^9R^{10}$ and $SR^9$; or $R^1$ and $R^2$ are joined to form a cyclic structure comprising a branched, unbranched or cyclic $C_1$-$C_{10}$ hydrocarbyl group wherein said hydrocarbyl group is optionally interrupted by up to 2 heteroatoms and optionally substituted by up to 3 groups independently selected from the group consisting of F, Cl, Br, I, $OR^9$, $OCOR^9$, $COOR^9$, CHO, $COR^9$, $CH_2OR^9$, $NR^9R^{10}$, $CH_2NR^9R^{10}$, $SR^9$, =O, =S and =NH;

$R^3$-$R^8$ are independently selected from the group consisting of H, F, Cl, Br, I, branched, unbranched or cyclic $C_1$-$C_{10}$ hydrocarbyl groups, $OR^9$, $OCOR^9$, $COOR^9$, CHO, $COR^9$, $CH_2OR^9$, $NR^9R^{10}$, $CH_2NR^9R^{10}$ and $SR^9$; or the pairs of substituents $R^3$ and $R^4$ together, $R^5$ and $R^6$ together, or $R^7$ and $R^8$ together are optionally independently selected from the group consisting of =O, =S and =NH;

B comprises a branched, unbranched or cyclic hydrocarbyl group of up to 30 carbon atoms optionally interrupted by up to 10 heteroatoms or a peptidyl chain of up to 20 amino acid residues, wherein B is optionally substituted with 1-5 groups selected from the group consisting of F, Cl, Br, I, =O, $OR^9$, $OCOR^9$, $COOR^9$, CN, $NR^9$, $NR^9R^{10}$, =S, and $SR^9$, provided that B comprises at least 3 atoms in a chain between group D and the group A;

Y is a functional group other than H, wherein Y is capable of bonding to a therapeutic or diagnostic agent molecule;

and $R^9$ and $R^{10}$ are independently selected from the group consisting of H, branched, unbranched and cyclic $C_1$-$C_{10}$ hydrocarbyl groups, and the salts thereof.

2. A compound represented by the following formula:

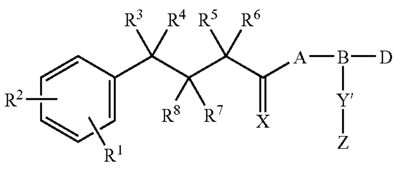

wherein X is O or S;

A is NH, O, S or $CR^9R^{10}$;

D is selected from the group consisting of $OPO_3H_2$, $PO_3H_2$, $OSO_3H$, $SO_3H$, COOH and the conjugate bases thereof;

$R^1$ and $R^2$ are independently selected from the group consisting of H, F, Cl, Br, I, branched, unbranched or cyclic $C_1$-$C_{10}$ hydrocarbyl groups, $OR^9$, $OCOR^9$, $COOR^9$, $CH_2OR^9$, CHO, $COR^9$, $NR^9R^{10}$ and $SR^9$; or $R^1$ and $R^2$ are joined to form a cyclic structure comprising a branched, unbranched or cyclic $C_1$-$C_{10}$ hydrocarbyl group wherein said hydrocarbyl group is optionally interrupted by up to 2 heteroatoms and optionally substituted by up to 3 groups independently selected from the group consisting of F, Cl, Br, I, $OR^9$, $OCOR^9$, $COOR^9$, CHO, $COR^9$, $CH_2OR^9$, $NR^9R^{10}$, $CH_2NR^9R^{10}$, $SR^9$, =O, =S and =NH;

$R^3$-$R^8$ are independently selected from the group consisting of H, F, Cl, Br, I, branched, unbranched or cyclic $C_1$-$C_{10}$ hydrocarbyl groups, $OR^9$, $OCOR^9$, $COOR^9$, CHO, $COR^9$, $CH_2OR^9$, $NR^9R^{10}$, $CH_2NR^9R^{10}$ and $SR^9$; or the pairs of substituents $R^3$ and $R^4$ together, $R^5$ and $R^6$ together, or $R^7$ and $R^8$ together are optionally independently selected from the group consisting of =O, =S and =NH;

B comprises a branched, unbranched or cyclic hydrocarbyl group of up to 30 carbon atoms optionally interrupted by up to 10 heteroatoms or a peptidyl chain of up to 20 amino acid residues, wherein B is optionally substituted with 1-5 groups selected from the group consisting of F, Cl, Br, I, =O, $OR^9$, $OCOR^9$, $COOR^9$, CN, $NR^9$, $NR^9R^{10}$, =S, and $SR^9$, provided that B comprises at least 3 atoms in a chain between group D and the group A;

wherein Y' is a residue of a functional group capable of bonding to a therapeutic or diagnostic agent molecule;

5. The compound of claim 1 wherein the hydrocarbyl groups are independently selected from the group consisting of alkyl, alkenyl, alkynyl, aryl and aralkyl.

6. The compound of claim 1 wherein $R^1$ and $R^2$ are independently selected from the group consisting of I, $CH_3$, Br and H.

7. The compound of claim 1 wherein $R^1$ is in the para position and is selected from the group consisting of I, Br and $CH_3$, and $R^2$ is H.

8. The compound of claim 1 wherein $R^3$-$R^8$ are H.

9. The compound of claim 1 wherein $R^9$ and $R^{10}$ are H.

10. The compound of claim 1 wherein Y is selected from the group consisting of $-NH_2$, -SH, -OH, -CHO, -NCS, and -NCO.

11. The compound of claim 1 wherein B-D comprises a moiety represented by Formula 5:

(Formula 5)

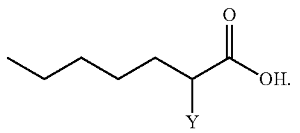

12. The compound of claim 1 wherein B-D comprises a moiety represented by Formula 6:

(Formula 6)

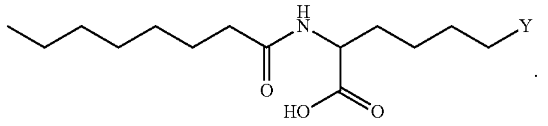

13. The compound of claim 1 represented by Formula 7:

(Formula 7)

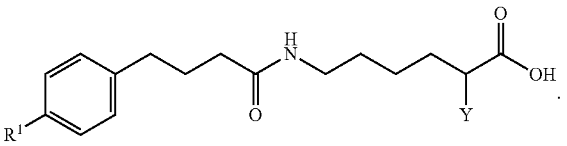

14. The compound of claim 1 represented by Formula 8:

(Formula 8)

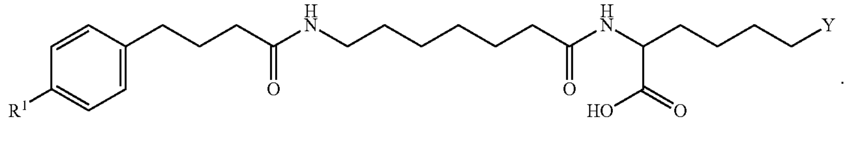

Z comprises the residue of a therapeutic or diagnostic agent molecule and optionally a linker; and $R^9$ and $R^{10}$ are independently selected from the group consisting of H, branched, unbranched and cyclic $C_1$-$C_{10}$ hydrocarbyl groups, and the salts thereof.

3. The compound of claim 1 wherein B comprises an amino acid residue.

4. The compound of claim 1 wherein B is cleavable by an enzyme.

15. The compound of claim 1 wherein Y is $-NH_2$.

16. The compound of claim 2 wherein Y' is selected from the group consisting of -NH-, -S-, -O-, -CO-, -NHCS-, -NHCO- and a bond.

17. The compound of claim 2 wherein B comprises a residue selected from the group 3-[2-(aminylethyl)dithio]propionyl, N-[α-maleimido-3'-yl-acetyl, N,N'-1,4-bis-maleimido-3',3"-diyl-butane, N,N'-1,6-bis-maleimido-3',3"-diyl-hexane, N,N'-1,2-bis-maleimido-3',3"-diyl-ethane, N,N'-1,4-bis-maleimido-3',3"-diyl-2,3-dihydroxybutane, N-[β-maleimido-3'-yl-propionyl, N-[β-3'-yl- semicarbazyl, N,N'-

1,8-bis-malimido-3,3'-diyl-trethyleneglycol, N,N'-1,11-bis-maleimido-3',3'-diyl-tetraethyleneglycol, suberyl, dimethyladipimidyl, dimethylpimelimidyl, dimethylsuberimidyl, 1,4-di-[3'-(2'-thiyl)-propionamido]butane, glutaryl, dithiobispropionyl, tartaryl, dimethyl 3,3'-dithiobispropionimidyl, 3,4-dithio-N,N'-1,6-bis-maleimido-3',3"-diyl-hexane, ethylene glycol bis-succinyl, N-7-maleimido-3'-yl-caproyl, N-7-maleimido-3'-yl-caproylsemicarbazyl, N-[γ-maleimido-3'-yl-butyryl, 1,6-hexane-bis-vinylsulfone, N-[κ-maleimido-3'-yl-undecanoyl, N-[κ-maleimido-3'-yl-undecanoylsemicarbazyl, 4-[N-maleimido-3'yl-methyl] cyclohexane-1-carboxy-[6-amidocaproyl], 6-[3-mercapto-] propionamidohexanoyl, m-[maleimido-3-yl]-benzoyl, 4-(4-N-maleimido-3'-ylphenyl)butyrylsemicarbazyl, adipyl, 3-mercapto-propionylsemicarbazyl, N-[p-maleimido-3-ylphenyl]ureyl, 2-mercaptoacetyl, 3-mercaptopropionyl, 3-[bromoacetamido]propionyl, 2-iodoacetyl, 4-[iodoacetyl] aminobenzoyl, 4-[N-maleimido-3'-ylmethyl]cyclohexane-1-carboxyl, 4-[p-maleimido-3'-yl]butyryl, 6-[β-maleimido-3-yl-propionamido]hexanoyl, and p-[2-mercaptoethyl] benzoyl, and 4-thiobutanimidamidyl.

18. The compound of claim 2 wherein B-D comprises a moiety represented by Formula 9:

(Formula 9)

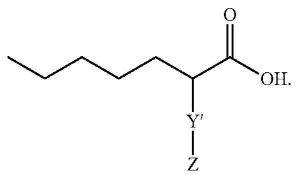

19. The compound of claim 2 wherein B-D comprises a moiety represented by Formula 10:

(Formula 10)

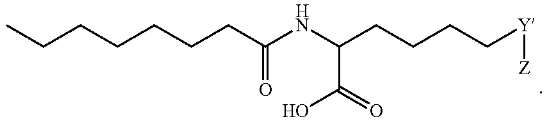

20. The compound of claim 2 comprising a moiety represented by Formula 11:

(Formula 11)

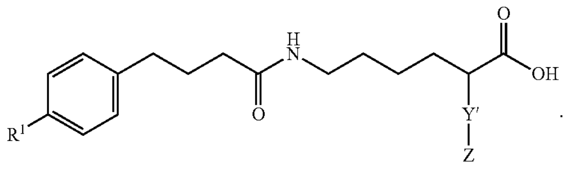

21. The compound of claim 2 comprising a moiety represented by Formula 12:

22. The compound of claim 2 wherein Y' is —NH—.

23. The compound of claim 2 wherein the therapeutic or diagnostic agent is an organic compound, a metalloorganic compound, a compound comprising a radionuclide, a nucleotide, a nucleic acid, a polymer, a peptide, a nucleopeptide, a protein, an antibody, a lipid, a steroid, or a derivative or combination of any thereof.

24. The compound of claim 2 wherein the therapeutic agent molecule is a drug for treating cancer, cardiovascular disease, obesity, viral, bacterial, fungal or other infections, inflammation, neurological disorders, degenerative neurological disorders, psychiatric diseases or conditions, depression, hormonal disorders, glucose metabolism disorders or diabetes, or a drug for contraception.

25. The compound of claim 2 wherein the therapeutic agent molecule is a drug for the treatment of a tumour characterised by a rapid uptake of albumin.

26. The compound of claim 2 wherein the therapeutic agent molecule is a drug for the treatment of a tumour with a doubling time of less than 60 days.

27. The compound of claim 2 wherein the therapeutic agent molecule is a drug for the treatment of colorectal, breast, prostate, lung, head-and-neck, pancreatic, stomach, or ovarian cancer, or of lymphomas, leukemias, astrocytomas, or of hepatocellular carcinomas.

28. The compound of claim 2 wherein the diagnostic agent molecule is an agent for diagnostic imaging techniques, fluorescence-based techniques, angiography, fluoroangiography, ultrasonography, magnetic resonance-based diagnostic procedures, magnetic resonance imaging, X-ray imaging, nuclear medicine, single photon emission computed tomography (SPECT) or positron emission tomography (PET).

29. The compound of claim 2 wherein the diagnostic agent molecule is a fluorophore for ophthalmological angiography or a contrast agent for X-ray or magnetic resonance imaging.

30. The compound of claim 2 wherein the diagnostic agent molecule comprises fluorescein, Gadolinium (III) - diethyltriaminepentaacetic acid (Gd-DTPA), or a residue thereof.

31. A pharmaceutical composition comprising a compound according to claim 1 and a pharmaceutically acceptable carrier.

32. A method of binding a therapeutic or diagnostic compound to albumin in a patient comprising the steps of (a) providing a conjugate comprising the albumin-binding compound of claim 1 conjugated to the therapeutic or diagnostic compound, and (b) administering a therapeutically effective amount of the conjugate to the patient.

33. A method of increasing the blood circulation time of a therapeutic or diagnostic compound in a patient comprising the steps of (a) providing a conjugate comprising the albumin-binding compound of claim 1 conjugated to the therapeutic or diagnostic compound, and (Formula 12)

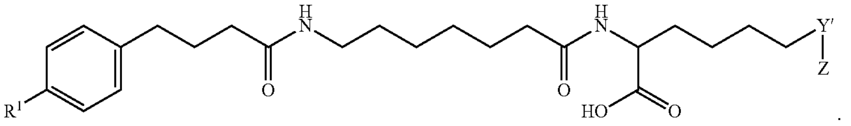

(b) administering a therapeutically effective amount of the conjugate to the patient.

34. A method of increasing the retention time of a therapeutic or diagnostic compound in the vascular space of a patient comprising the steps of (a) providing a conjugate comprising the albumin-binding compound of claim 1 conjugated to the therapeutic or diagnostic compound, and (b) administering a therapeutically effective amount of the conjugate to the patient.

35. A method of improving the tissue penetration capacity of a therapeutic or diagnostic compound in a patient comprising the steps of (a) providing a conjugate comprising the albumin-binding compound of claim 1 conjugated to the therapeutic or diagnostic compound, and (b) administering a therapeutically effective amount of the conjugate to the patient.

36. A method of lowering the effective dose of a therapeutic or diagnostic compound comprising conjugating the therapeutic or diagnostic compound to the albumin-binding compound of claim 1, wherein the conjugate is effective in a patient at a lower dose compared to the unconjugated therapeutic or diagnostic compound.

* * * * *